(12) United States Patent
Berry et al.

(10) Patent No.: US 11,919,938 B2
(45) Date of Patent: Mar. 5, 2024

(54) IMMUNOASSAYS AND ENGINEERED PROTEINS FOR MONITORING ANTIBODY TREATMENTS TO THE IMMUNE CHECKPOINT INHIBITORS PD1 AND PD-L1

(71) Applicant: GRIFOLS DIAGNOSTIC SOLUTIONS INC., Emeryville, CA (US)

(72) Inventors: Jody Berry, Easton, PA (US); Elizabeth Antony Booth, Berkeley, CA (US); Joyee Antony George, Alameda, CA (US); Elisabete Nascimento, Burlingame, CA (US); Daniel Nagore Casas, Derio (ES)

(73) Assignee: GRIFOLS DIAGNOSTIC SOLUTIONS INC., Emeryville, CA (US)

( * ) Notice: Subject to any disclaimer, the term of this patent is extended or adjusted under 35 U.S.C. 154(b) by 513 days.

(21) Appl. No.: 16/321,385

(22) PCT Filed: Nov. 29, 2018

(86) PCT No.: PCT/IB2018/059449
§ 371 (c)(1),
(2) Date: Jan. 28, 2019

(87) PCT Pub. No.: WO2019/106592
PCT Pub. Date: Jun. 6, 2019

(65) Prior Publication Data
US 2020/0299353 A1 Sep. 24, 2020

Related U.S. Application Data

(60) Provisional application No. 62/593,080, filed on Nov. 30, 2017.

(51) Int. Cl.
*C07K 14/705* (2006.01)
*G01N 33/68* (2006.01)

(52) U.S. Cl.
CPC .. *C07K 14/70521* (2013.01); *C07K 14/70503* (2013.01); *C07K 14/70532* (2013.01); *G01N 33/6854* (2013.01); *C07K 2319/02* (2013.01); *C07K 2319/21* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,288,931 A * | 2/1994 | Chang | C07K 1/1133 435/69.1 |
| 7,029,674 B2 * | 4/2006 | Carreno | A61P 37/06 424/130.1 |
| 7,112,660 B1 * | 9/2006 | Domingues | C07K 14/5406 530/351 |
| 7,449,188 B2 | 11/2008 | De Filette et al. | |
| 8,119,770 B2 | 2/2012 | Blanche et al. | |
| 2003/0045474 A1 * | 3/2003 | Sailer | A61P 19/00 514/8.8 |
| 2012/0328693 A1 | 12/2012 | Lan et al. | |
| 2014/0079701 A1 * | 3/2014 | Miller | C07K 16/241 435/69.6 |
| 2014/0154743 A1 * | 6/2014 | Levy | C07K 16/00 435/69.6 |
| 2019/0345225 A1 * | 11/2019 | Seehra | A61P 5/50 |

FOREIGN PATENT DOCUMENTS

| | | |
|---|---|---|
| CN | 101830986 A | 9/2010 |
| CN | 105 999 223 A | 10/2016 |
| EP | 0 827 544 B1 | 8/2004 |
| EP | 2 092 069 A2 | 8/2009 |
| EP | 3 147 298 A1 | 3/2017 |
| JP | 2010-510801 A | 4/2010 |
| WO | WO 2011/161699 A2 | 12/2011 |
| WO | WO 2015/195531 A2 * | 12/2015 |
| WO | WO 2016/014688 A2 * | 1/2016 |
| WO | WO 2017/058115 A1 | 4/2017 |

OTHER PUBLICATIONS

Tokuriki et al., 2009, Curr. Opin. Struc. Biol. 19:596-604.*
Fenton et al. (2020, Medicinal Chemistry Research 29:1133-1146).*
Bhattacharya et al. (2017, PLoS One 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Liu et al. (2015, Arthritis Research & Therapy 17:340 [DOI 10.1186/s13075-015-0859-z, pp. 1-13]).*
Agrawal et al., "Nivolumab dose selection: challenges, opportunities, and lessons learned for cancer immunotherapy", Journal for ImmunoTherapy of Cancer, vol. 4, No. 72, pp. 1-11, 2016.

(Continued)

*Primary Examiner* — Elizabeth C. Kemmerer
(74) *Attorney, Agent, or Firm* — Knobbe, Martens, Olson & Bear LLP

(57) ABSTRACT

Fusion proteins comprising an extracellular domain of PD1 (programmed cell death protein-1) protein and/or an extracellular domain of PD-L1 (programmed cell death-ligand 1 protein (CD274 or B7-H1)) protein. Portions of the extracellular domains are expressed in specific configurations and purified as protein and used in immunoassays to monitor the circulating levels of biotherapeutic antibodies to these proteins. Also described is a method of determining the amount of circulating levels of a biotherapeutic antibody in a biological sample obtained from a patient, wherein a patient has undergone at least one dose of immunotherapy.

7 Claims, 7 Drawing Sheets
Specification includes a Sequence Listing.

(56) References Cited

OTHER PUBLICATIONS

Brahmer et al., "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, vol. 28, No. 19 pp. 3167-3175, 2010.
Dempke et al. "Second- and third-generation drugs for immuno-oncology treatment—The more the better?", European Journal of Cancer, vol. 74, pp. 55-72., 2017.
Elassaiss-Schaap et al., "Using Model-Based "Learn and Confirm" to Reveal the Pharmacokinetics-Pharmacodynamics Relationship of Pembrolizumab in the Keynote-001 Trial", CPT Pharmacometrics Syst. Pharmacol., vol. 6, No. 1, pp. 1-8, 2017.
Farolfi et al., "Pharmacokinetics, pharmacodynamics and clinical efficacy of nivolumab in the treatment of metastatic renal cell carcinoma", Expert Opinion Drug Metabolism & Toxicology, vol. 12, No. 9, pp. 1089-1096, 2016.
"FDA approves Opdivo to treat advanced form of kidney cancer", U.S. Food & Drug Administration [press announcement]. Retrieved from https://www.fda.gov/NewsEvents/Newsroom/PressAnnouncements/ucm473971.htm, in 3 pages, 2015.
"FDA expands approved use of Opdivo to treat lung cancer", U.S. Food & Drug Administration [press announcement]. Retrieved from https://www.fda.gov/NewsEvents/newsroom/PressAnnouncements/ucm436534.htm, 2014.
"FDA grants accelerated approval to pembrolizumab for first tissue/site agnostic indication" U.S. Food & Drug Administration [press announcement]. Retrieved from https://www.fda.gov/Drugs/InformationOnDrugs/ApprovedDrugs/ucm560040.htm, in 2 pages, 2017.
Gardiner et al., "A Randomized, Double-Blind, Placebo-Controlled Assessment of BMS-936558, a Fully Human Monoclonal Antibody to Programmed Death-1 (PD-1), in Patients with Chronic Hepatitis C Virus Infection", PLoS One, vol. 8, No. 5 pp. 1-11, 2013.
Goodman et al., "PD-1—PD-L1 immune-checkpoint blockade in B-cell lymphomas", Nature Reviews Clinical Oncology, vol. 14, pp. 203-220, 2017.
Jefferis et al., "Human immunoglobulin allotypes: Possible implications for immunogenicity", mAbs, vol. 1, No. 4, pp. 332-338, 2009.
Lee et al., "Structural bassi of checkpoint blockade by monoclonal antibodies in cancer immunotherapy" Nature Communications, vol. 7 in 10 pages, 2016.
Lee et al., "Solution structure of the tetrameric minimum transforming domain of p53", Nature Structural Biology, vol. 1, pp. 877-890, 1994.
Lui et al., "Soluble PD-1 aggravates progression of collagen-induced arthritis through Th1 and Th17 pathways", Arthritis Research & Therapy, vol. 17, No. 340 in 13 pages, 2015.
Ono Pharmaceutical Co. Ltd., "Human Anti-human PD-1 Monoclonal Antibody "Opdivo® Intravenous Infusion 20 mg/100 mg" Receives Manufacturing and Marketing Approval in Japan for the Treatment of Unresectable Melanoma", FirstWord Pharma [press release], Retrieved from https://www.firstwordpharma.com/node/1222697?tsid=17, in 3 pages, 2014.
Opdivo®, Bristol-Meyers Squibb (2016), (nivolumab) Granted First Approval of a PD-1 Inhibitor in Hematology for the Treatment of Classical Hodgkin Lymphoma Patients Who Have Relapsed or Progressed After Auto-HSCT and Post-transplantation Brentuximab Vedotin by the FDA1 [press release]. Retrieved from https://news.brns.com/press-release/cancer/opdivo-nivolumab-granted-first-approval-pd-1-inhibitor-hematology-treatment-cla in 7 pages.
Opdivo (package insert), Bristol-Meyers Squibb, New York, NY in 73 pages, 2017.
Pembrolizumab (package insert), Merck, Kelinworth, NJ in 46 pages, 2017.
Sica et al., "B7-H4, a Molecule of the B7 Family, Negatively Regulates T Cell Immunity", Immunity, vol. 18, pp. 849-861, 2003.
Ternant et al., "IgG1 Allotypes Influence the Pharmacokinetics of Therapeutic Monoclonal Antibodies through FcRn Binding", The Journal of Immunology, vol. 196, No. 2, pp. 607-613, 2016.
Thompson et al., "Costimulatory B7-H1 in renal cell carcinoma patients: Indicator of tumor aggressiveness and potential therapeutic target", PNAS USA, vol. 101, No. 49, pp. 17174-17179, 2004.
Webster et al., "A comparison of the ability of the human IgG1 allotypes G1m3 and G1m1, 17 to stimulate T-cell responses from allotype matched and mismatched donors", mAbs, vol. 8, No. 2, pp. 253-263, 2016.
Yamamoto et al., "Phase I study of Nivolumab, an anti-PD-1 antibody, in patients with malignant solid tumors", Invest New Drugs, vol. 35, pp. 207-216, 2017.
Yang et al., "Highly Stable Trimers Formed by Human Immunodeficiency Virus Type 1 Envelope Glycoproteins Fused with the Trimeric Motif of T4 Bacteriophage Fibritin" Journal of Virology, vol. 76, No. 9, pp. 4634-4642, 2002.
Ybe et al., "Nuclear localization of clathrin involves a labile helix outside the trimerization domain", FEBS Letters, vol. 587, No. 2, pp. 142-149, 2013.
Zheng et al., "Level of circulating PD-L1 expression in patients with advanced gastric cancer and its clinical implications", Chinese Journal of Cancer Research, vol. 26, No. 1, pp. 104-111, 2014.
International Search Report and Written Opinion, dated May 31, 2019, in International Application No. PCT/IB2018/059449.
Schaefer et al., Minibodies, Antibody engineering, pp. 85-99, 2010.
Pluckthun et al New Protein Engineering Approaching to Multivalent and Bispecific Antibody Fragments, Immunotechnology, vol. 3, No. 2, pp. 95-96, 1997.
Song et al. Protective Effects of FC-fused PD-L1 on Two Different Animal Models of Colitis, vol. 64, No. 2, pp. 260-270, 2015.

* cited by examiner

1. MW standards, 10 µL
2. 1. HuIL2SS-PD1(GGGGS)2-Murine IgG1(CH2,CH3 ONLY), 5 µL
3. 2. HuIL2SS-PD1 (GGGPS)2- Murine IgG1(CH2, CH3 ONLY), 4.5 µL
4. 3.>HuIL2SS-PD1 - murine IgG1 Fc, 6.3 µL
5. 4.>HuIL2SS-PD1-murine IgG2A Fc, 2.8 µL
6. 5.>HuIL2SS-PDL1(GGGGS)2-Murine IgG1(CH2,CH3 ONLY), 10 µL
7. 6.>HuIL2SS-PDL1(GGGPS)2-Murine IgG1(CH2,CH3 ONLY), 5 µL
8. 7.>HuIL2SS-PDL1-murine IgG1 Fc, 20 µL
9. 8.>HuIL2SS-Nivolumab with Synagis Fc HC/LC, 20 µL
10. 9.>HuIL2SS-Pembrolizumab with Synagis Fc HC/LC, 20 µL 1. MW standards, 10 μL
2. 1. HuIL2SS-PD1(GGGGS)2-Murine IgG1(CH2,CH3 ONLY), 4 μg
3. 2. HuIL2SS-PD1 (GGGPS)2- Murine IgG1(CH2, CH3 ONLY), 4 μg
4. 3.>HuIL2SS-PD1 - murine IgG1 Fc, 4 μg
5. 4.>HuIL2SS-PD1-murine IgG2A Fc, 4 μg
6. 5.>HuIL2SS-PDL1(GGGGS)2-Murine IgG1(CH2,CH3 ONLY), 4 μg
7. 6.>HuIL2SS-PDL1(GGGPS)2-Murine IgG1(CH2,CH3 ONLY), 4 μg
8. 7.>HuIL2SS-PDL1-murine IgG1 Fc, 0.2 μg
9. 8.>HuIL2SS-Nivolumab with Synagis Fc HC/LC, 1.6 μg
10. 9.>HuIL2SS-Pembrolizumab with Synagis Fc HC/LC, 0.4 μg

SEQUENCE LISTING

```
<160> NUMBER OF SEQ ID NOS: 31

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Ser Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
```

```
                180                 185                 190
Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270
```

```
Gly Ile Gln Asp Thr Asn Ser Lys Lys Gln Ser Asp Thr His Leu Glu
            275                 280                 285

Glu Thr
    290

<210> SEQ ID NO 3
<211> LENGTH: 20
<212> TYPE: PRT
<213> ORGANISM: Artificial Sequence
<220> FEATURE:
<223> OTHER INFORMATION: Synthetic; Human IL2 signal peptide

<400> SEQUENCE: 3

Met Tyr Arg Met Gln Leu Leu Ser Cys Ile Ala Leu Ser Leu Ala Leu
1               5                   10                  15

Val Thr Asn Ser
            20

<210> SEQ ID NO 4
<211> LENGTH: 4
<212> TYPE: PRT
<213> ORGANISM: Artificial Sequence
<220> FEATURE:
<223> OTHER INFORMATION: Synthetic; Gly-Ser linker

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: Synthetic; Gly-Pro-Ser linker (Flex Pro Linker)

<400> SEQUENCE: 5

Gly Gly Gly Pro Ser
1               5

<210> SEQ ID NO 6
<211> LENGTH: 214
<212> TYPE: PRT
<213> ORGANISM: Artificial Sequence
<220> FEATURE:
<223> OTHER INFORMATION: Synthetic; Murine IgG 1 containing CH2 and CH3
      domains only

<400> SEQUENCE: 6

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys Gly Arg Pro Lys Ala
            100                 105                 110
```

```
Pro Gln Val Tyr Thr Ile Pro Pro Lys Glu Gln Met Ala Lys Asp
            115                 120                 125
Lys Val Ser Leu Thr Cys Met Ile Thr Asp Phe Phe Pro Glu Asp Ile
130                 135                 140
Thr Val Glu Trp Gln Trp Asn Gly Gln Pro Ala Glu Asn Tyr Lys Asn
145                 150                 155                 160
Thr Gln Pro Ile Met Asp Thr Asp Gly Ser Tyr Phe Val Tyr Ser Lys
                165                 170                 175
Leu Asn Val Gln Lys Ser Asn Trp Glu Ala Gly Asn Thr Phe Thr Cys
            180                 185                 190
Ser Val Leu His Glu Gly Leu His Asn His His Thr Glu Lys Ser Leu
            195                 200                 205
Ser His Ser Pro Gly Ile
            210

<210> SEQ ID NO 7
<211> LENGTH: 227
<212> TYPE: PRT
<213> ORGANISM: Artificial Sequence
<220> FEATURE:
<223> OTHER INFORMATION: Synthetic; Murine IgG1 containing Fe region

<400> SEQUENCE: 7

Val Pro Arg Asp Cys Gly Cys Lys Pro Cys Ile Cys Thr Val Pro Glu
1               5                   10                  15
Val Ser Ser Val Phe Ile Phe Pro Pro Lys Pro Lys Asp Val Leu Thr
            20                  25                  30
Ile Thr Leu Thr Pro Lys Val Thr Cys Val Val Val Asp Ile Ser Lys
        35                  40                  45
Asp Asp Pro Glu Val Gln Phe Ser Trp Phe Val Asp Asp Val Glu Val
50                  55                  60
His Thr Ala Gln Thr Gln Pro Arg Glu Glu Gln Phe Asn Ser Thr Phe
65                  70                  75                  80
Arg Ser Val Ser Glu Leu Pro Ile Met His Gln Asp Trp Leu Asn Gly
                85                  90                  95
Lys Glu Phe Lys Cys Arg Val Asn Ser Ala Ala Phe Pro Ala Pro Ile
            100                 105                 110
Glu Lys Thr Ile Ser Lys Thr Lys Gly Arg Pro Lys Ala Pro Gln Val
            115                 120                 125
Tyr Thr Ile Pro Pro Lys Glu Gln Met Ala Lys Asp Lys Val Ser
            130                 135                 140
Leu Thr Cys Met Ile Thr Asp Phe Phe Pro Glu Asp Ile Thr Val Glu
145                 150                 155                 160
Trp Gln Trp Asn Gly Gln Pro Ala Glu Asn Tyr Lys Asn Thr Gln Pro
                165                 170                 175
Ile Met Asp Thr Asp Gly Ser Tyr Phe Val Tyr Ser Lys Leu Asn Val
                180                 185                 190
Gln Lys Ser Asn Trp Glu Ala Gly Asn Thr Phe Thr Cys Ser Val Leu
            195                 200                 205
His Glu Gly Leu His Asn His His Thr Glu Lys Ser Leu Ser His Ser
            210                 215                 220
Pro Gly Ile
225

<210> SEQ ID NO 8
```

<211> LENGTH: 232
<212> TYPE: PRT
<213> ORGANISM: Artificial Sequence
<220> FEATURE:
<223> OTHER INFORMATION: Synthetic; Murine IgG2A containing Fe region

<400> SEQUENCE: 8

```
Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Glu Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His His Thr Thr Lys
    210                 215                 220

Ser Phe Ser Arg Thr Pro Gly Lys
225                 230
```

<210> SEQ ID NO 9
<211> LENGTH: 27
<212> TYPE: PRT
<213> ORGANISM: Artificial Sequence
<220> FEATURE:
<223> OTHER INFORMATION: Synthetic; GCN4 trimer domain

<400> SEQUENCE: 9

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

<210> SEQ ID NO 10
<211> LENGTH: 94
<212> TYPE: PRT
<213> ORGANISM: Artificial Sequence
<220> FEATURE:
<223> OTHER INFORMATION: Synthetic; Clathrin trimer domain

<400> SEQUENCE: 10

-continued

Gly Ser His Met Trp Lys Gln Ser Val Glu Leu Ala Lys Lys Asp Ser
1               5                   10                  15

Leu Tyr Lys Asp Ala Met Gln Tyr Ala Ser Glu Ser Lys Asp Thr Glu
            20                  25                  30

Leu Ala Glu Glu Leu Leu Gln Trp Phe Leu Gln Glu Glu Lys Arg Glu
        35                  40                  45

Cys Phe Gly Ala Cys Leu Phe Thr Cys Tyr Asp Leu Leu Arg Pro Asp
    50                  55                  60

Val Val Leu Glu Leu Ala Trp Arg His Asn Ile Met Asp Phe Ala Met
65                  70                  75                  80

Pro Tyr Phe Ile Gln Val Met Lys Glu Tyr Leu Thr Lys Val
                85                  90

<210> SEQ ID NO 11
<211> LENGTH: 40
<212> TYPE: PRT
<213> ORGANISM: Artificial Sequence
<220> FEATURE:
<223> OTHER INFORMATION: Synthetic; p53 tetramer domain

<400> SEQUENCE: 11

Lys Pro Leu Asp Gly Glu Tyr Phe Thr Leu Gln Ile Arg Gly Arg Glu
1               5                   10                  15

Arg Phe Glu Met Phe Arg Glu Leu Asn Glu Ala Leu Glu Leu Lys Asp
            20                  25                  30

Ala Gln Ala Gly Lys Glu Pro Gly
        35                  40

<210> SEQ ID NO 12
<211> LENGTH: 118
<212> TYPE: PRT
<213> ORGANISM: Homo sapiens

<400> SEQUENCE: 12

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val
            100                 105                 110

Thr Glu Arg Arg Ala Glu
        115

<210> SEQ ID NO 13
<211> LENGTH: 117
<212> TYPE: PRT
<213> ORGANISM: Homo sapiens

<400> SEQUENCE: 13

Ala Phe Thr Val Thr Val Pro Lys Asp Leu Tyr Val Val Glu Tyr Gly
1               5                   10                  15

```
Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr
            115

<210> SEQ ID NO 14
<211> LENGTH: 362
<212> TYPE: PRT
<213> ORGANISM: Artificial Sequence
<220> FEATURE:
<223> OTHER INFORMATION: Synthetic; PD-1 fusion protein

<400> SEQUENCE: 14

Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Gly Gly Gly Gly Ser Gly
    130                 135                 140

Gly Gly Gly Ser Val Pro Glu Val Ser Val Phe Ile Phe Pro Pro
145                 150                 155                 160

Lys Pro Lys Asp Val Leu Thr Ile Thr Leu Thr Pro Lys Val Thr Cys
                165                 170                 175

Val Val Val Asp Ile Ser Lys Asp Asp Pro Glu Val Gln Phe Ser Trp
            180                 185                 190

Phe Val Asp Asp Val Glu Val His Thr Ala Gln Thr Gln Pro Arg Glu
        195                 200                 205

Glu Gln Phe Asn Ser Thr Phe Arg Ser Val Ser Glu Leu Pro Ile Met
    210                 215                 220

His Gln Asp Trp Leu Asn Gly Lys Glu Phe Lys Cys Arg Val Asn Ser
225                 230                 235                 240

Ala Ala Phe Pro Ala Pro Ile Glu Lys Thr Ile Ser Lys Thr Lys Gly
                245                 250                 255
```

```
Arg Pro Lys Ala Pro Gln Val Tyr Thr Ile Pro Pro Lys Glu Gln
            260                 265                 270

Met Ala Lys Asp Lys Val Ser Leu Thr Cys Met Ile Thr Asp Phe Phe
            275                 280                 285

Pro Glu Asp Ile Thr Val Glu Trp Gln Trp Asn Gly Gln Pro Ala Glu
            290                 295                 300

Asn Tyr Lys Asn Thr Gln Pro Ile Met Asp Thr Asp Gly Ser Tyr Phe
305                 310                 315                 320

Val Tyr Ser Lys Leu Asn Val Gln Lys Ser Asn Trp Glu Ala Gly Asn
                325                 330                 335

Thr Phe Thr Cys Ser Val Leu His Glu Gly Leu His Asn His His Thr
            340                 345                 350

Glu Lys Ser Leu Ser His Ser Pro Gly Ile
            355                 360

<210> SEQ ID NO 15
<211> LENGTH: 362
<212> TYPE: PRT
<213> ORGANISM: Artificial Sequence
<220> FEATURE:
<223> OTHER INFORMATION: Synthetic; PD-1 fusion protein

<400> SEQUENCE: 15

Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Gly Gly Pro Ser Gly
    130                 135                 140

Gly Gly Pro Ser Val Pro Glu Val Ser Ser Val Phe Ile Phe Pro Pro
145                 150                 155                 160

Lys Pro Lys Asp Val Leu Thr Ile Thr Leu Thr Pro Lys Val Thr Cys
                165                 170                 175

Val Val Val Asp Ile Ser Lys Asp Asp Pro Glu Val Gln Phe Ser Trp
            180                 185                 190

Phe Val Asp Asp Val Glu Val His Thr Ala Gln Thr Gln Pro Arg Glu
        195                 200                 205

Glu Gln Phe Asn Ser Thr Phe Arg Ser Val Ser Glu Leu Pro Ile Met
    210                 215                 220

His Gln Asp Trp Leu Asn Gly Lys Glu Phe Lys Cys Arg Val Asn Ser
225                 230                 235                 240

Ala Ala Phe Pro Ala Pro Ile Glu Lys Thr Ile Ser Lys Thr Lys Gly
                245                 250                 255
```

```
Arg Pro Lys Ala Pro Gln Val Tyr Thr Ile Pro Pro Lys Glu Gln
            260                 265                 270

Met Ala Lys Asp Lys Val Ser Leu Thr Cys Met Ile Thr Asp Phe Phe
        275                 280                 285

Pro Glu Asp Ile Thr Val Glu Trp Gln Trp Asn Gly Gln Pro Ala Glu
    290                 295                 300

Asn Tyr Lys Asn Thr Gln Pro Ile Met Asp Thr Asp Gly Ser Tyr Phe
305                 310                 315                 320

Val Tyr Ser Lys Leu Asn Val Gln Lys Ser Asn Trp Glu Ala Gly Asn
                325                 330                 335

Thr Phe Thr Cys Ser Val Leu His Glu Gly Leu His Asn His His Thr
            340                 345                 350

Glu Lys Ser Leu Ser His Ser Pro Gly Ile
            355                 360

<210> SEQ ID NO 16
<211> LENGTH: 365
<212> TYPE: PRT
<213> ORGANISM: Artificial Sequence
<220> FEATURE:
<223> OTHER INFORMATION: Synthetic; PD-1 fusion protein

<400> SEQUENCE: 16

Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Val Pro Arg Asp Cys Gly
    130                 135                 140

Cys Lys Pro Cys Ile Cys Thr Val Pro Glu Val Ser Ser Val Phe Ile
145                 150                 155                 160

Phe Pro Pro Lys Pro Lys Asp Val Leu Thr Ile Thr Leu Thr Pro Lys
                165                 170                 175

Val Thr Cys Val Val Val Asp Ile Ser Lys Asp Asp Pro Glu Val Gln
            180                 185                 190

Phe Ser Trp Phe Val Asp Asp Val Glu Val His Thr Ala Gln Thr Gln
        195                 200                 205

Pro Arg Glu Glu Gln Phe Asn Ser Thr Phe Arg Ser Val Ser Glu Leu
    210                 215                 220

Pro Ile Met His Gln Asp Trp Leu Asn Gly Lys Glu Phe Lys Cys Arg
225                 230                 235                 240

Val Asn Ser Ala Ala Phe Pro Ala Pro Ile Glu Lys Thr Ile Ser Lys
                245                 250                 255
```

```
Thr Lys Gly Arg Pro Lys Ala Pro Gln Val Tyr Thr Ile Pro Pro Pro
            260                 265                 270

Lys Glu Gln Met Ala Lys Asp Lys Val Ser Leu Thr Cys Met Ile Thr
        275                 280                 285

Asp Phe Phe Pro Glu Asp Ile Thr Val Glu Trp Gln Trp Asn Gly Gln
    290                 295                 300

Pro Ala Glu Asn Tyr Lys Asn Thr Gln Pro Ile Met Asp Thr Asp Gly
305                 310                 315                 320

Ser Tyr Phe Val Tyr Ser Lys Leu Asn Val Gln Lys Ser Asn Trp Glu
                325                 330                 335

Ala Gly Asn Thr Phe Thr Cys Ser Val Leu His Glu Gly Leu His Asn
                340                 345                 350

His His Thr Glu Lys Ser Leu Ser His Ser Pro Gly Ile
            355                 360                 365

<210> SEQ ID NO 17
<211> LENGTH: 370
<212> TYPE: PRT
<213> ORGANISM: Artificial Sequence
<220> FEATURE:
<223> OTHER INFORMATION: Synthetic; PD-1 fusion protein

<400> SEQUENCE: 17

Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Pro Arg Gly Pro Thr Ile
    130                 135                 140

Lys Pro Cys Pro Pro Cys Lys Cys Pro Ala Pro Asn Leu Leu Gly Gly
145                 150                 155                 160

Pro Ser Val Phe Ile Phe Pro Pro Lys Ile Lys Asp Val Leu Met Ile
                165                 170                 175

Ser Leu Ser Pro Ile Val Thr Cys Val Val Asp Val Ser Glu Asp
            180                 185                 190

Asp Pro Asp Val Gln Ile Ser Trp Phe Val Asn Asn Val Glu Val His
        195                 200                 205

Thr Ala Gln Thr Gln Thr His Arg Glu Asp Tyr Asn Ser Thr Leu Arg
    210                 215                 220

Val Val Ser Ala Leu Pro Ile Gln His Gln Asp Trp Met Ser Gly Lys
225                 230                 235                 240

Glu Phe Lys Cys Lys Val Asn Asn Lys Asp Leu Pro Ala Pro Ile Glu
                245                 250                 255
```

```
Arg Thr Ile Ser Lys Pro Lys Gly Ser Val Arg Ala Pro Gln Val Tyr
        260                 265                 270

Val Leu Pro Pro Glu Glu Glu Met Thr Lys Lys Gln Val Thr Leu
        275                 280                 285

Thr Cys Met Val Thr Asp Phe Met Pro Glu Asp Ile Tyr Val Glu Trp
        290                 295                 300

Thr Asn Asn Gly Lys Thr Glu Leu Asn Tyr Lys Asn Thr Glu Pro Val
305                 310                 315                 320

Leu Asp Ser Asp Gly Ser Tyr Phe Met Tyr Ser Lys Leu Arg Val Glu
                325                 330                 335

Lys Lys Asn Trp Val Glu Arg Asn Ser Tyr Ser Cys Ser Val Val His
                340                 345                 350

Glu Gly Leu His Asn His His Thr Thr Lys Ser Phe Ser Arg Thr Pro
        355                 360                 365

Gly Lys
    370

<210> SEQ ID NO 18
<211> LENGTH: 171
<212> TYPE: PRT
<213> ORGANISM: Artificial Sequence
<220> FEATURE:
<223> OTHER INFORMATION: Synthetic; PD-1 fusion protein

<400> SEQUENCE: 18

Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Gly Tyr Ile Pro Glu Ala
    130                 135                 140

Pro Arg Asp Gly Gln Ala Tyr Val Arg Lys Asp Gly Glu Trp Val Leu
145                 150                 155                 160

Leu Ser Thr Phe Leu His His His His His His
                165                 170

<210> SEQ ID NO 19
<211> LENGTH: 238
<212> TYPE: PRT
<213> ORGANISM: Artificial Sequence
<220> FEATURE:
<223> OTHER INFORMATION: Synthetic; PD-1 fusion protein

<400> SEQUENCE: 19

Met Tyr Arg Met Gln Leu Leu Ser Cys Ile Ala Leu Ser Leu Ala Leu
```

```
            1               5                  10                 15
Val Thr Asn Ser Asn Pro Pro Thr Phe Ser Pro Ala Leu Leu Val Val
                    20                  25                 30

Thr Glu Gly Asp Asn Ala Thr Phe Thr Cys Ser Phe Ser Asn Thr Ser
                    35                  40                 45

Glu Ser Phe Val Leu Asn Trp Tyr Arg Met Ser Pro Ser Asn Gln Thr
        50                  55                 60

Asp Lys Leu Ala Ala Phe Pro Glu Asp Arg Ser Gln Pro Gly Gln Asp
65                  70                  75                 80

Ser Arg Phe Arg Val Thr Gln Leu Pro Asn Gly Arg Asp Phe His Met
                    85                  90                 95

Ser Val Val Arg Ala Arg Arg Asn Asp Ser Gly Thr Tyr Leu Cys Gly
                    100                 105                110

Ala Ile Ser Leu Ala Pro Lys Ala Gln Ile Lys Glu Ser Leu Arg Ala
                    115                 120                125

Glu Leu Arg Val Thr Glu Arg Arg Ala Glu Gly Ser His Met Trp Lys
        130                 135                140

Gln Ser Val Glu Leu Ala Lys Lys Asp Ser Leu Tyr Lys Asp Ala Met
145                 150                 155                160

Gln Tyr Ala Ser Glu Ser Lys Asp Thr Glu Leu Ala Glu Glu Leu Leu
                    165                 170                175

Gln Trp Phe Leu Gln Glu Glu Lys Arg Glu Cys Phe Gly Ala Cys Leu
                    180                 185                190

Phe Thr Cys Tyr Asp Leu Leu Arg Pro Asp Val Val Leu Glu Leu Ala
                    195                 200                205

Trp Arg His Asn Ile Met Asp Phe Ala Met Pro Tyr Phe Ile Gln Val
        210                 215                220

Met Lys Glu Tyr Leu Thr Lys Val His His His His His
225                 230                 235
```

<210> SEQ ID NO 20
<211> LENGTH: 185
<212> TYPE: PRT
<213> ORGANISM: Artificial Sequence
<220> FEATURE:
<223> OTHER INFORMATION: Synthetic; PD-1 fusion protein

<400> SEQUENCE: 20

```
Met Tyr Arg Met Gln Leu Leu Ser Cys Ile Ala Leu Ser Leu Ala Leu
1               5                   10                 15

Val Thr Asn Ser Asn Pro Pro Thr Phe Ser Pro Ala Leu Leu Val Val
                    20                  25                 30

Thr Glu Gly Asp Asn Ala Thr Phe Thr Cys Ser Phe Ser Asn Thr Ser
                    35                  40                 45

Glu Ser Phe Val Leu Asn Trp Tyr Arg Met Ser Pro Ser Asn Gln Thr
        50                  55                 60

Asp Lys Leu Ala Ala Phe Pro Glu Asp Arg Ser Gln Pro Gly Gln Asp
65                  70                  75                 80

Ser Arg Phe Arg Val Thr Gln Leu Pro Asn Gly Arg Asp Phe His Met
                    85                  90                 95

Ser Val Val Arg Ala Arg Arg Asn Asp Ser Gly Thr Tyr Leu Cys Gly
                    100                 105                110

Ala Ile Ser Leu Ala Pro Lys Ala Gln Ile Lys Glu Ser Leu Arg Ala
                    115                 120                125

Glu Leu Arg Val Thr Glu Arg Arg Ala Glu Lys Pro Leu Asp Gly Glu
```

```
            130                 135                 140
Tyr Phe Thr Leu Gln Ile Arg Gly Arg Glu Arg Phe Glu Met Phe Arg
145                 150                 155                 160

Glu Leu Asn Glu Ala Leu Glu Leu Lys Asp Ala Gln Ala Gly Lys Glu
                165                 170                 175

Pro Gly His His His His His His
            180                 185
```

<210> SEQ ID NO 21
<211> LENGTH: 361
<212> TYPE: PRT
<213> ORGANISM: Artificial Sequence
<220> FEATURE:
<223> OTHER INFORMATION: Synthetic; PD-L1 fusion protein

<400> SEQUENCE: 21

```
Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
                20                  25                  30

Val Glu Tyr Gly Ser Asn Met Thr Ile Glu Cys Lys Phe Pro Val Glu
            35                  40                  45

Lys Gln Leu Asp Leu Ala Ala Leu Ile Val Tyr Trp Glu Met Glu Asp
        50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Gly Gly Gly Ser Gly Gly
            130                 135                 140

Gly Gly Ser Val Pro Glu Val Ser Ser Val Phe Ile Phe Pro Pro Lys
145                 150                 155                 160

Pro Lys Asp Val Leu Thr Ile Thr Leu Thr Pro Lys Val Thr Cys Val
                165                 170                 175

Val Val Asp Ile Ser Lys Asp Asp Pro Glu Val Gln Phe Ser Trp Phe
            180                 185                 190

Val Asp Asp Val Glu Val His Thr Ala Gln Thr Gln Pro Arg Glu Glu
        195                 200                 205

Gln Phe Asn Ser Thr Phe Arg Ser Val Ser Glu Leu Pro Ile Met His
    210                 215                 220

Gln Asp Trp Leu Asn Gly Lys Glu Phe Lys Cys Arg Val Asn Ser Ala
225                 230                 235                 240

Ala Phe Pro Ala Pro Ile Glu Lys Thr Ile Ser Lys Thr Lys Gly Arg
                245                 250                 255

Pro Lys Ala Pro Gln Val Tyr Thr Ile Pro Pro Lys Glu Gln Met
            260                 265                 270

Ala Lys Asp Lys Val Ser Leu Thr Cys Met Ile Thr Asp Phe Phe Pro
        275                 280                 285

Glu Asp Ile Thr Val Glu Trp Gln Trp Asn Gly Gln Pro Ala Glu Asn
    290                 295                 300

Tyr Lys Asn Thr Gln Pro Ile Met Asp Thr Asp Gly Ser Tyr Phe Val
```

305                 310                 315                 320

Tyr Ser Lys Leu Asn Val Gln Lys Ser Asn Trp Glu Ala Gly Asn Thr
                325                 330                 335

Phe Thr Cys Ser Val Leu His Glu Gly Leu His Asn His His Thr Glu
                340                 345                 350

Lys Ser Leu Ser His Ser Pro Gly Ile
                355                 360

<210> SEQ ID NO 22
<211> LENGTH: 361
<212> TYPE: PRT
<213> ORGANISM: Artificial Sequence
<220> FEATURE:
<223> OTHER INFORMATION: Synthetic; PD-L1 fusion protein

<400> SEQUENCE: 22

Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
                20                  25                  30

Val Glu Tyr Gly Ser Asn Met Thr Ile Glu Cys Lys Phe Pro Val Glu
            35                  40                  45

Lys Gln Leu Asp Leu Ala Ala Leu Ile Val Tyr Trp Glu Met Glu Asp
        50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Gly Gly Gly Pro Ser Gly Gly
    130                 135                 140

Gly Pro Ser Val Pro Glu Val Ser Ser Val Phe Ile Phe Pro Pro Lys
145                 150                 155                 160

Pro Lys Asp Val Leu Thr Ile Thr Leu Thr Pro Lys Val Thr Cys Val
                165                 170                 175

Val Val Asp Ile Ser Lys Asp Asp Pro Glu Val Gln Phe Ser Trp Phe
            180                 185                 190

Val Asp Asp Val Glu Val His Thr Ala Gln Thr Gln Pro Arg Glu Glu
        195                 200                 205

Gln Phe Asn Ser Thr Phe Arg Ser Val Ser Glu Leu Pro Ile Met His
    210                 215                 220

Gln Asp Trp Leu Asn Gly Lys Glu Phe Lys Cys Arg Val Asn Ser Ala
225                 230                 235                 240

Ala Phe Pro Ala Pro Ile Glu Lys Thr Ile Ser Lys Thr Lys Gly Arg
                245                 250                 255

Pro Lys Ala Pro Gln Val Tyr Thr Ile Pro Pro Lys Glu Gln Met
            260                 265                 270

Ala Lys Asp Lys Val Ser Leu Thr Cys Met Ile Thr Asp Phe Phe Pro
        275                 280                 285

Glu Asp Ile Thr Val Glu Trp Gln Trp Asn Gly Gln Pro Ala Glu Asn
    290                 295                 300

Tyr Lys Asn Thr Gln Pro Ile Met Asp Thr Asp Gly Ser Tyr Phe Val

```
305                 310                 315                 320
Tyr Ser Lys Leu Asn Val Gln Lys Ser Asn Trp Glu Ala Gly Asn Thr
                325                 330                 335

Phe Thr Cys Ser Val Leu His Glu Gly Leu His Asn His His Thr Glu
            340                 345                 350

Lys Ser Leu Ser His Ser Pro Gly Ile
            355                 360

<210> SEQ ID NO 23
<211> LENGTH: 364
<212> TYPE: PRT
<213> ORGANISM: Artificial Sequence
<220> FEATURE:
<223> OTHER INFORMATION: Synthetic; PD-L1 fusion protein

<400> SEQUENCE: 23

Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
            20                  25                  30

Val Glu Tyr Gly Ser Asn Met Thr Ile Glu Cys Lys Phe Pro Val Glu
        35                  40                  45

Lys Gln Leu Asp Leu Ala Ala Leu Ile Val Tyr Trp Glu Met Glu Asp
    50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Val Pro Arg Asp Cys Gly Cys
    130                 135                 140

Lys Pro Cys Ile Cys Thr Val Pro Glu Val Ser Ser Val Phe Ile Phe
145                 150                 155                 160

Pro Pro Lys Pro Lys Asp Val Leu Thr Ile Thr Leu Thr Pro Lys Val
                165                 170                 175

Thr Cys Val Val Val Asp Ile Ser Lys Asp Asp Pro Glu Val Gln Phe
            180                 185                 190

Ser Trp Phe Val Asp Asp Val Glu Val His Thr Ala Gln Thr Gln Pro
        195                 200                 205

Arg Glu Glu Gln Phe Asn Ser Thr Phe Arg Ser Val Ser Glu Leu Pro
    210                 215                 220

Ile Met His Gln Asp Trp Leu Asn Gly Lys Glu Phe Lys Cys Arg Val
225                 230                 235                 240

Asn Ser Ala Ala Phe Pro Ala Pro Ile Glu Lys Thr Ile Ser Lys Thr
                245                 250                 255

Lys Gly Arg Pro Lys Ala Pro Gln Val Tyr Thr Ile Pro Pro Pro Lys
            260                 265                 270

Glu Gln Met Ala Lys Asp Lys Val Ser Leu Thr Cys Met Ile Thr Asp
        275                 280                 285

Phe Phe Pro Glu Asp Ile Thr Val Glu Trp Gln Trp Asn Gly Gln Pro
    290                 295                 300

Ala Glu Asn Tyr Lys Asn Thr Gln Pro Ile Met Asp Thr Asp Gly Ser
```

```
                    305                 310                 315                 320
Tyr Phe Val Tyr Ser Lys Leu Asn Val Gln Lys Ser Asn Trp Glu Ala
                325                 330                 335

Gly Asn Thr Phe Thr Cys Ser Val Leu His Glu Gly Leu His Asn His
                340                 345                 350

His Thr Glu Lys Ser Leu Ser His Ser Pro Gly Ile
                355                 360

<210> SEQ ID NO 24
<211> LENGTH: 369
<212> TYPE: PRT
<213> ORGANISM: Artificial Sequence
<220> FEATURE:
<223> OTHER INFORMATION: Synthetic; PD-L1 fusion protein

<400> SEQUENCE: 24

Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
                20                  25                  30

Val Glu Tyr Gly Ser Asn Met Thr Ile Glu Cys Lys Phe Pro Val Glu
            35                  40                  45

Lys Gln Leu Asp Leu Ala Ala Leu Ile Val Tyr Trp Glu Met Glu Asp
        50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Pro Arg Gly Pro Thr Ile Lys
    130                 135                 140

Pro Cys Pro Pro Cys Lys Cys Pro Ala Pro Asn Leu Leu Gly Gly Pro
145                 150                 155                 160

Ser Val Phe Ile Phe Pro Pro Lys Ile Lys Asp Val Leu Met Ile Ser
                165                 170                 175

Leu Ser Pro Ile Val Thr Cys Val Val Val Asp Val Ser Glu Asp Asp
            180                 185                 190

Pro Asp Val Gln Ile Ser Trp Phe Val Asn Asn Val Glu Val His Thr
        195                 200                 205

Ala Gln Thr Gln Thr His Arg Glu Asp Tyr Asn Ser Thr Leu Arg Val
    210                 215                 220

Val Ser Ala Leu Pro Ile Gln His Gln Asp Trp Met Ser Gly Lys Glu
225                 230                 235                 240

Phe Lys Cys Lys Val Asn Asn Lys Asp Leu Pro Ala Pro Ile Glu Arg
                245                 250                 255

Thr Ile Ser Lys Pro Lys Gly Ser Val Arg Ala Pro Gln Val Tyr Val
            260                 265                 270

Leu Pro Pro Pro Glu Glu Glu Met Thr Lys Lys Gln Val Thr Leu Thr
        275                 280                 285

Cys Met Val Thr Asp Phe Met Pro Glu Asp Ile Tyr Val Glu Trp Thr
    290                 295                 300

Asn Asn Gly Lys Thr Glu Leu Asn Tyr Lys Asn Thr Glu Pro Val Leu
```

```
                305                 310                 315                 320
Asp Ser Asp Gly Ser Tyr Phe Met Tyr Ser Lys Leu Arg Val Glu Lys
            325                 330                 335

Lys Asn Trp Val Glu Arg Asn Ser Tyr Ser Cys Ser Val Val His Glu
            340                 345                 350

Gly Leu His Asn His His Thr Thr Lys Ser Phe Ser Arg Thr Pro Gly
            355                 360                 365

Lys

<210> SEQ ID NO 25
<211> LENGTH: 170
<212> TYPE: PRT
<213> ORGANISM: Artificial Sequence
<220> FEATURE:
<223> OTHER INFORMATION: Synthetic; PD-L1 fusion protein

<400> SEQUENCE: 25

Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
            20                  25                  30

Val Glu Tyr Gly Ser Asn Met Thr Ile Glu Cys Lys Phe Pro Val Glu
        35                  40                  45

Lys Gln Leu Asp Leu Ala Ala Leu Ile Val Tyr Trp Glu Met Glu Asp
50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Gly Tyr Ile Pro Glu Ala Pro
130                 135                 140

Arg Asp Gly Gln Ala Tyr Val Arg Lys Asp Gly Glu Trp Val Leu Leu
145                 150                 155                 160

Ser Thr Phe Leu His His His His His
                165                 170

<210> SEQ ID NO 26
<211> LENGTH: 237
<212> TYPE: PRT
<213> ORGANISM: Artificial Sequence
<220> FEATURE:
<223> OTHER INFORMATION: Synthetic; PD-L1 fusion protein

<400> SEQUENCE: 26

Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
            20                  25                  30

Val Glu Tyr Gly Ser Asn Met Thr Ile Glu Cys Lys Phe Pro Val Glu
        35                  40                  45

Lys Gln Leu Asp Leu Ala Ala Leu Ile Val Tyr Trp Glu Met Glu Asp
50                  55                  60

Lys Asn Ile Ile Gln Phe Val His Gly Glu Glu Asp Leu Lys Val Gln
```

```
                65                  70                  75                  80
        His Ser Ser Tyr Arg Gln Arg Ala Arg Leu Leu Lys Asp Gln Leu Ser
                        85                  90                  95

Leu Gly Asn Ala Ala Leu Gln Ile Thr Asp Val Lys Leu Gln Asp Ala
                    100                 105                 110

Gly Val Tyr Arg Cys Met Ile Ser Tyr Gly Gly Ala Asp Tyr Lys Arg
                    115                 120                 125

Ile Thr Val Lys Val Asn Ala Pro Tyr Gly Ser His Met Trp Lys Gln
            130                 135                 140

Ser Val Glu Leu Ala Lys Lys Asp Ser Leu Tyr Lys Asp Ala Met Gln
        145                 150                 155                 160

Tyr Ala Ser Glu Ser Lys Asp Thr Glu Leu Ala Glu Glu Leu Leu Gln
                        165                 170                 175

Trp Phe Leu Gln Glu Glu Lys Arg Glu Cys Phe Gly Ala Cys Leu Phe
                    180                 185                 190

Thr Cys Tyr Asp Leu Leu Arg Pro Asp Val Val Leu Glu Leu Ala Trp
                    195                 200                 205

Arg His Asn Ile Met Asp Phe Ala Met Pro Tyr Phe Ile Gln Val Met
            210                 215                 220

Lys Glu Tyr Leu Thr Lys Val His His His His His His
        225                 230                 235
```

<210> SEQ ID NO 27
<211> LENGTH: 184
<212> TYPE: PRT
<213> ORGANISM: Artificial Sequence
<220> FEATURE:
<223> OTHER INFORMATION: Synthetic; PD-L1 fusion protein

<400> SEQUENCE: 27

```
        Met Tyr Arg Met Gln Leu Leu Ser Cys Ile Ala Leu Ser Leu Ala Leu
        1               5                   10                  15

Val Thr Asn Ser Ala Phe Thr Val Thr Val Pro Lys Asp Leu Tyr Val
                    20                  25                  30

Val Glu Tyr Gly Ser Asn Met Thr Ile Glu Cys Lys Phe Pro Val Glu
                35                  40                  45

Lys Gln Leu Asp Leu Ala Ala Leu Ile Val Tyr Trp Glu Met Glu Asp
            50                  55                  60

Lys Asn Ile Ile Gln Phe Val His Gly Glu Glu Asp Leu Lys Val Gln
        65                  70                  75                  80

His Ser Ser Tyr Arg Gln Arg Ala Arg Leu Leu Lys Asp Gln Leu Ser
                        85                  90                  95

Leu Gly Asn Ala Ala Leu Gln Ile Thr Asp Val Lys Leu Gln Asp Ala
                    100                 105                 110

Gly Val Tyr Arg Cys Met Ile Ser Tyr Gly Gly Ala Asp Tyr Lys Arg
                    115                 120                 125

Ile Thr Val Lys Val Asn Ala Pro Tyr Lys Pro Leu Asp Gly Glu Tyr
            130                 135                 140

Phe Thr Leu Gln Ile Arg Gly Arg Glu Arg Phe Glu Met Phe Arg Glu
        145                 150                 155                 160

Leu Asn Glu Ala Leu Glu Leu Lys Asp Ala Gln Ala Gly Lys Glu Pro
                        165                 170                 175

Gly His His His His His His
                    180
```

<210> SEQ ID NO 28
<211> LENGTH: 217
<212> TYPE: PRT
<213> ORGANISM: Artificial Sequence
<220> FEATURE:
<223> OTHER INFORMATION: Synthetic; Murine IgG2A

<400> SEQUENCE: 28

```
Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys Gly Ser
            100                 105                 110

Val Arg Ala Pro Gln Val Tyr Val Leu Pro Pro Pro Glu Glu Glu Met
        115                 120                 125

Thr Lys Lys Gln Val Thr Leu Thr Cys Met Val Thr Asp Phe Met Pro
    130                 135                 140

Glu Asp Ile Tyr Val Glu Trp Thr Asn Asn Gly Lys Thr Glu Leu Asn
145                 150                 155                 160

Tyr Lys Asn Thr Glu Pro Val Leu Asp Ser Asp Gly Ser Tyr Phe Met
                165                 170                 175

Tyr Ser Lys Leu Arg Val Glu Lys Lys Asn Trp Val Glu Arg Asn Ser
            180                 185                 190

Tyr Ser Cys Ser Val Val His Glu Gly Leu His Asn His His Thr Thr
        195                 200                 205

Lys Ser Phe Ser Arg Thr Pro Gly Lys
    210                 215
```

<210> SEQ ID NO 29
<211> LENGTH: 195
<212> TYPE: PRT
<213> ORGANISM: Artificial Sequence
<220> FEATURE:
<223> OTHER INFORMATION: Synthetic; PD-1 fusion protein

<400> SEQUENCE: 29

```
Met Tyr Arg Met Gln Leu Leu Ser Cys Ile Ala Leu Ser Leu Ala Leu
1               5                   10                  15

Val Thr Asn Ser Asn Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95
```

```
Ser Val Val Arg Ala Arg Arg Asn Asp Ser Gly Thr Tyr Leu Cys Gly
                100                 105                 110

Ala Ile Ser Leu Ala Pro Lys Ala Gln Ile Lys Glu Ser Leu Arg Ala
            115                 120                 125

Glu Leu Arg Val Thr Glu Arg Arg Ala Glu Gly Gly Pro Ser Gly
        130                 135                 140

Gly Gly Pro Ser Lys Pro Leu Asp Gly Glu Tyr Phe Thr Leu Gln Ile
145                 150                 155                 160

Arg Gly Arg Glu Arg Phe Glu Met Phe Arg Glu Leu Asn Glu Ala Leu
                165                 170                 175

Glu Leu Lys Asp Ala Gln Ala Gly Lys Glu Pro Gly His His His His
            180                 185                 190

His His His
        195
```

<210> SEQ ID NO 30
<211> LENGTH: 194
<212> TYPE: PRT
<213> ORGANISM: Artificial Sequence
<220> FEATURE:
<223> OTHER INFORMATION: Synthetic; PD-L1 fusion protein

<400> SEQUENCE: 30

```
Met Tyr Arg Met Gln Leu Leu Ser Cys Ile Ala Leu Ser Leu Ala Leu
1               5                   10                  15

Val Thr Asn Ser Ala Phe Thr Val Thr Val Pro Lys Asp Leu Tyr Val
            20                  25                  30

Val Glu Tyr Gly Ser Asn Met Thr Ile Glu Cys Lys Phe Pro Val Glu
        35                  40                  45

Lys Gln Leu Asp Leu Ala Ala Leu Ile Val Tyr Trp Glu Met Glu Asp
50                  55                  60

Lys Asn Ile Ile Gln Phe Val His Gly Glu Glu Asp Leu Lys Val Gln
65                  70                  75                  80

His Ser Ser Tyr Arg Gln Arg Ala Arg Leu Leu Lys Asp Gln Leu Ser
                85                  90                  95

Leu Gly Asn Ala Ala Leu Gln Ile Thr Asp Val Lys Leu Gln Asp Ala
            100                 105                 110

Gly Val Tyr Arg Cys Met Ile Ser Tyr Gly Gly Ala Asp Tyr Lys Arg
        115                 120                 125

Ile Thr Val Lys Val Asn Ala Pro Tyr Gly Gly Pro Ser Gly Gly
    130                 135                 140

Gly Pro Ser Lys Pro Leu Asp Gly Glu Tyr Phe Thr Leu Gln Ile Arg
145                 150                 155                 160

Gly Arg Glu Arg Phe Glu Met Phe Arg Glu Leu Asn Glu Ala Leu Glu
                165                 170                 175

Leu Lys Asp Ala Gln Ala Gly Lys Glu Pro Gly His His His His His
            180                 185                 190

His His
```

```
<210> SEQ ID NO 31
<211> LENGTH: 7
<212> TYPE: PRT
<213> ORGANISM: Artificial Sequence
<220> FEATURE:
<223> OTHER INFORMATION: Synthetic; polyhistidine tag

<400> SEQUENCE: 31

His His His His His His His
1               5
```

IMMUNOASSAYS AND ENGINEERED PROTEINS FOR MONITORING ANTIBODY TREATMENTS TO THE IMMUNE CHECKPOINT INHIBITORS PD1 AND PD-L1

PRIORITY AND CROSS REFERENCE TO RELATED APPLICATIONS

This application is the U.S. National Stage Application under 35 U.S.C. § 371 of International Application No. PCT/IB2018/059449, filed Nov. 29, 2018, designating the U.S. and published in English as WO 2019/106592 A2 on Jun. 6, 2019, which claims the benefit of U.S. Provisional Application No. 62/593,080, filed Nov. 30, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application includes an Electronic Sequence Listing as an ASCII text file submitted via EFS-Web. The Electronic Sequence Listing is provided as a file entitled DURC048007APCREPLACEMENTSEQLIST.txt, created on Dec. 2, 2021 and last modified on Dec. 2, 2021, which is 58,591 bytes in size. The information in the Electronic Sequence Listing is incorporated herein by reference in its entirety.

TECHNICAL FIELD

This application relates to fusion proteins comprising extracellular domain of PD-1 (programmed cell death-1 protein) and/or fusion proteins comprising extracellular domain of PD-L1 (programmed cell death-ligand 1 protein) (CD274 or B7-H1). Portions of the extracellular domains are expressed in specific configurations and purified as protein and used in immunoassays to monitor the circulating levels of biotherapeutic antibodies to these proteins. Also described herein are methods for detecting and monitoring a therapeutic antibody in a biological sample obtained from a patient, wherein a patient has undergone at least one dose of immunotherapy.

BACKGROUND

Programmed cell death 1 (PD-1) receptor, one of the most studied immune checkpoint targets, is expressed on the surface of activated immune cell types, including T cells, B cells, natural killer (NK)/natural killer T (NKT) cells and others[1]. Multiple therapeutic monoclonal antibodies (mAbs) targeting PD-1 and PD-L1 are on the market and more than a dozen traditional and bispecific mAbs are being reviewed at the FDA and EMA.

PD-1 is a negative regulator of T-cell activity and the interaction of PD-1 with one of its ligands, PD-L1, at the tumor surface produces a checkpoint blockade decreasing the ability of activated T cells to produce an effective immune response. The expression of high levels of PD-L1 on tumor cell surfaces, permits escape from the anti-tumor responses by suppressing T cell functions, including cytotoxic activity. Therapeutic antibodies that target either PD-1 or PD-L1 will block the ligand-receptor interaction, and restore immune function to the tumor microenvironment. The use of these mAbs has yielded exciting clinical responses across many cancer types and a growing number of these mAbs have now entered clinical development.

Due to the novelty of targeting the immunological checkpoint blockade activated by cancer cells, optimal dose and schedule for administering these mAbs and the tools necessary to determine these parameters have not been fully developed. While current anti-PD-1 mAb therapeutic regimens have shown promising results, it will be necessary to define more accurate and personalized, dosing regimens to increase efficacy and decrease cost. Steady state antibody levels can vary up to 10-fold for the same antibody regimen, and even more so when sub-therapeutic dosing is used[2-4]. These studies could optimize treatment while decreasing cost burden and adverse event incidence. A large number of immuno-modulatory mAbs are under review by the FDA and EU, many on a fast track basis, further highlighting the need for tests which measure circulating levels of PD-1 and PD-L1 targeted mAbs. The immunoassays under development will provide effective guidance of treatment regimens, particularly given (1) the gross variation observed in steady state mAb levels both within and across disease indications[2-4] and (2) the varying progression states that are observed in patients under these therapies[1,3,6].

Measuring anti-PD-1 and anti-PD-L1 levels has potential importance not only in determining optimal dosing for different tumors or molecular pathologies, but also to gauge whether circulating levels may explain or predict adverse events known to occur following remission. There is an unmet need because no monitoring programs currently exist and more data is required to evaluate and determine dosing schedules and obviate unnecessary immunotoxicity and cost.

Nivolumab is a humanized IgG4 anti-PD-1 mAb. Nivolumab works as a checkpoint inhibitor, blocking a negative regulator that would have prevented activated T cells from attacking the cancer, thus allowing the immune system to clear the cancer. It was discovered at Medarex, developed by Medarex and Ono Pharmaceutical, and brought to market by Bristol-Myers Squibb (which acquired Medarex in 2009) and Ono.

Nivolumab (Opdivo®), is a biotherapeutic mAb used to treat cancer and first approved by the Japanese authorities in 2014[6] and by the FDA also in 2014[7]. It is used as a front-line treatment for inoperable or metastatic skin melanoma. It is used differentially in combination with ipilimumab (mAb against CTLA-4, cytotoxic T-lymphocyte associated protein-4) if the cancer does or does not have a mutation in BRAF. It is considered to be used as a second-line treatment for squamous non-small cell lung cancer (NSCLC)[8], and as a second-line treatment for renal cell carcinomas and in May 2016 was approved for recalcitrant classical Hodgkin Lymphoma.[9] It is being tested for many other cancers and likely will have greatly expanded uses.

Merck produces a similar mAb therapy pembrolizumab (Keytruda), also an IgG4 class mAb against PD-1, which was also approved in 2014. As of 2017, pembrolizumab is used via intravenous infusion to treat inoperable or metastatic melanoma, metastatic NSCLC in certain situations, as a second-line treatment for head and neck squamous cell carcinoma, refractory classical Hodgkin's lymphoma. For NSCLC, Pembrolizumab is a first line treatment if the cancer overexpresses PD-L1 and the cancer has no mutations in EGFR or in ALK; assessment of PD-L1 must be conducted with a validated and approved companion diagnostic. Moreover, Pembrolizumab is the first drug approved by the FDA based on the presence of a biomarker (PD-1) instead of the targeted tissue.[10] Many other anti-PD-1 and anti-PD-L1 biotherapeutic antibodies are in the clinic now and include alternative formats such as bispecifics, DARTs (Dual Anti-CTLA-4 & Anti-PD-1 blockade in Rare Tumors) and BiTes (Bispecific T cell engagers).

Conversely, upregulation of PD-L1 allows cancers to evade the host immune system and high tumor expression of PD-L1 is associated with increased tumor aggressiveness and a 4.5-fold increased risk of death.[11] In addition to the PD-L1 inhibitors already approved for treatment, many PD-L1 are in development as immuno-oncology therapies and are showing promising results in clinical trials including Atezolizumab and Avelumab.

These drugs increase the efficacy of T cells which are able to more aggressively attack and kill cancer cells. For Nivolumab, in some cases there are severe side effects that include immune-related inflammation of the lungs, colon, liver, kidneys, and thyroid; and effects on skin, central nervous system, heart, and digestive system.[12] For Pembrolizumab, patients have developed severe infusion-related reactions and adverse effects including lung inflammation (some fatal) and inflammation of endocrine organs that caused inflammation (pituitary gland, thyroid (causing both hypothyroidism and hyperthyroidism in different patients), and pancreatitis that caused Type 1 diabetes and diabetic ketoacidosis) resulting in some patients going on lifelong hormone therapy (e.g. insulin therapy or thyroid hormones). Patients have also developed colon, liver, and kidney inflammation due to the mAb drug.[13] Many other symptoms and malaise are reported for both.

Patients who show these side effects are taken off the mAb drugs, then put back on the drug if/when the side effects subside. It is possible that the doses being used could be titered or greatly reduced if the level in a patient were monitored. However, there are currently no monitoring assays available for testing the circulating mAb drug levels and no antigens for these tests have been qualified.

SUMMARY

The present application provides fusion proteins related to programmed cell death 1 (PD-1) and programmed cell death-ligand (PD-L1) proteins. The fusion protein can be a recombinant protein comprising either a modification of the natural protein and/or a fusion protein comprised of another domain with distinct properties to improve function in a diagnostic assay.

One aspect described herein provides a recombinant protein comprising a PD-1 protein fused to an oligomerization domain. Another aspect described herein provides a fusion protein comprising a PD-1 protein fused to oligomerization domains. Another aspect described herein provides a recombinant protein comprising a PD-L1 protein fused to an oligomerization domain. Another aspect described herein provides a fusion protein comprising a PD-L1 protein fused to oligomerization domains. Yet another aspect described herein provides a fusion protein comprising PD-1 and PD-L1 protein fused to an oligomerization domain. In some embodiments, the fusion protein is a recombinant protein.

The PD-1 and/or PD-L1 proteins may be from multiple species or from a single species. In one aspect, the PD-1 and/or PD-L1 protein(s) is a human PD-1 and/or human PD-L1 protein(s). In another aspect, the fusion protein comprises the extracellular domain of the PD-1 and/or PD-L1 protein or a fragment thereof. In one embodiment, the fusion protein comprises an immunoglobulin-like domain of the extracellular domain of the PD-1. In another embodiment, the fusion protein comprises an immunoglobulin-like domain of the extracellular domain of the PD-L1.

The PD-1 and/or PD-L1 extracellular domain(s) or a fragment thereof may comprise various modified proteins or peptides. The modification may be substitution, deletion or addition of at least one amino acid in wild-type PD-1 and/or PD-L1, as long as it does not change the function of PD-1 and PD-L1. Such various proteins or peptides may have a sequence homology of 70%, 75%, 80%, 85%, 90%, 91%, 92%, 93%, 94%, 95%, 96%, 97%, 98% or 99% to the wild-type protein.

The fusion proteins described herein comprise an extracellular domain of PD-1 or PD-L1 proteins, or a fragment thereof, and an oligomerization domain.

In some aspects, the fusion protein described herein comprises an extracellular domain of PD-1 protein, or a fragment thereof, and an oligomerization domain, wherein the oligomerization domain is selected from the group consisting of a murine IgG1 Fc domain, a murine IgG2A Fc domain, a GCN4 trimer domain, a clathrin trimer domain, and a p53 tetramer domain, or a fragment thereof.

In other aspects, the fusion protein described herein comprises an extracellular domain of PD-L1 protein, or a fragment thereof, and an oligomerization domain, wherein the oligomerization domain is selected from the group consisting of a murine IgG1 Fc domain, a murine IgG2A Fc domain, a GCN4 trimer domain, a clathrin trimer domain, and a p53 tetramer domain, or a fragment thereof.

The oligomerization domain described herein may comprise a domain selected from the group consisting of Clathrin, GCN4 trimerization domains, the p53 tetramerization domain, and pentameric domains. In some aspects, the oligomerization domain may comprise an Fc domain, a fragment of an Fc domain, and a variant of an Fc domain. In one embodiment, the PD-1 and/or PD-L1 protein is fused to the C-terminus of said Fc domain, or fragment thereof. In another embodiment, the PD-1 and/or PD-L1 protein is fused to the N-terminus of said Fc domain, or fragment thereof. In one embodiment, the Fc domain may be of human or mouse immunoglobulin. In another embodiment, the oligomerization domain may comprise an Fc fragment of mouse IgG1 or mouse IgG2A, or fragments thereof.

In some aspects, the oligomerization domain of the fusion protein described herein is a murine IgG1 Fc domain or a murine IgG2A Fc domain. In some aspects, the murine IgG1 Fc domain or the murine IgG2A Fc domain comprises a hinge region.

Fusion proteins that comprise an extracellular domain of PD-1 protein, or a fragment thereof, and an oligomerization domain, as described herein, may comprise a murine IgG1 Fc domain or a murine IgG2A Fc domain which comprises a hinge region.

Fusion proteins that comprise an extracellular domain of PD-L1 protein, or a fragment thereof, and an oligomerization domain, as described herein, may comprise a murine IgG1 Fc domain or a murine IgG2A Fc domain which comprises a hinge region.

The fusion protein described herein can be part of a higher order structure, such as a protein or multimeric complex. This can be either through intentional design of the protein with multimerization domains or inherently, via unexpected properties of the recombinant protein. In some aspects, the PD-1 and/or PD-L1 protein, or the fragment thereof, is fused to the oligomerization domain, via one or more peptide linkers. In some aspects, the extracellular domain of PD-1 protein, or the fragment thereof, is fused to the oligomerization domain, via one or more peptide linkers. In some aspects, the extracellular domain of PD-L1 protein, or the fragment thereof, is fused to the oligomerization domain, via one or more peptide linkers. In some aspects, the PD-1 and/or PD-L1 protein is fused to the Fc domain, or fragment thereof, via one or more peptide linkers. In some aspects, in the fusion proteins described herein, the extracellular domain of PD-1 protein, or the fragment thereof, is fused to the oligomerization domain via one or more flex linkers comprising amino acids Glycine and Serine or via one or more flex pro linkers comprising amino acids Glycine, Proline, and Serine. In some aspects, said one or more peptide linkers comprise the amino acid sequence set forth in SEQ ID NO: 4 or SEQ ID NO: 5. In some aspects, in the fusion proteins described herein, the extracellular domain of PD-L1 protein, or the fragment thereof, is fused to the oligomerization domain via one or more flex linkers comprising amino acids Glycine and Serine or via one or more flex pro linkers comprising amino acids Glycine, Proline, and Serine. In some aspects, said one or more peptide linkers comprise the amino acid sequence set forth in SEQ ID NO: 4 or SEQ ID NO: 5.

In some embodiments, the fusion proteins may comprise the amino acid sequence set forth in SEQ ID NOs: 14-27 or SEQ ID NOs: 29-30.

Other aspects of the present invention include fusion proteins as described herein, further comprising a signal sequence, wherein the signal sequence is fused at the N-terminus of the extracellular domain of PD-1 protein or the fragment thereof. Other aspects of the present invention include fusion proteins as described herein, further comprising a signal sequence, wherein the signal sequence is fused at the N-terminus of the extracellular domain of PD-L1 protein or the fragment thereof.

In some aspects the signal sequence comprises the amino acid sequence set forth in SEQ ID NO: 3. In other aspects, the amino acid sequence of the signal sequence shares at least 70% homology with the amino acid sequence set forth in SEQ ID NO: 3.

In some aspects of the present invention, the fusion protein described herein comprises an extracellular domain of PD-1 which amino acid sequence shares at least 70% homology with the amino acid sequence consisting of residues 21 to 170, 21 to 145, 33 to 170, 33 to 145, 35 to 170 or 35 to 145 of SEQ ID NO:1. In some aspects, the fusion protein comprises an extracellular domain of PD-1 which amino acid sequence shares at least 70% homology with the amino acid sequence consisting of residues 21 to 170 of SEQ ID NO:1. In some aspects, the fusion protein comprises an extracellular domain of PD-1 which amino acid sequence consists of residues 21 to 170 of SEQ ID NO:1.

In other aspects of the present invention, the fusion protein described herein comprises an extracellular domain of PD-L1 which amino acid sequence shares at least 70% homology with the amino acid sequence consisting of residues 18 to 239, 18 to 238, 18 to 225, 18 to 134, 18 to 127, 19 to 239, 19 to 238, 19 to 225, 19 to 134, 19 to 127, 133 to 225, 133 to 238, or 133 to 239 of SEQ ID NO: 2. In some aspects, the fusion protein comprises an extracellular domain of PD-L1 which amino acid sequence shares at least 70% homology with the amino acid sequence consisting of residues 18 to 239 of SEQ ID NO:2. In some aspects, the fusion protein comprises an extracellular domain of PD-L1 which amino acid sequence consists of residues 18 to 239 of SEQ ID NO:2.

In yet another aspect, the fusion protein as described herein comprises an extracellular domain of PD-1 which amino acid sequence comprises a sequence with at least 70% homology with the amino acid sequence set forth in SEQ ID NO: 12.

In yet another aspect, the fusion protein as described herein comprises an extracellular domain of PD-L1 which amino acid sequence comprises a sequence with at least 70% homology with the amino acid sequence set forth in SEQ ID NO: 22.

The fusion protein according to the present invention may comprise an extracellular domain of PD-1, or fragment thereof, and an oligomerization domain which amino acid sequence is selected from the group consisting of SEQ ID NO: 6, SEQ ID NO: 7, SEQ ID NO: 8, SEQ ID NO: 9, SEQ ID NO: 10, SEQ ID NO: 11, and SEQ ID NO:28.

The fusion protein according to the present invention may comprise an extracellular domain of PD-L1, or fragment thereof, and an oligomerization domain which amino acid sequence is selected from the group consisting of SEQ ID NO: 6, SEQ ID NO: 7, SEQ ID NO: 8, SEQ ID NO: 9, SEQ ID NO: 10, SEQ ID NO: 11, and SEQ ID NO:28.

In some aspects, the amino acid sequence of the fusion protein described herein is selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 29. In some aspects, the amino acid sequence of the fusion protein described herein is selected from the group consisting of the amino acid sequence that shares at least 70% homology with the amino acid sequence set forth in SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 29.

In some aspects, the amino acid sequence of the fusion protein described herein is selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 30. In some aspects, the amino acid sequence of the fusion protein described herein is selected from the group consisting of the amino acid sequence that shares at least 70% homology with the amino acid sequence set forth in SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 30.

Some aspects of the present invention relate to fusion proteins as described herein wherein the PD-1 is recombinant PD-1. Yet other aspects of the present invention relate to fusion proteins as described herein wherein the PD-1 is recombinant human PD-1.

Some aspects of the present invention relate to fusion proteins as described herein wherein the PD-L1 is recombinant PD-L1. Yet other aspects of the present invention relate to fusion proteins as described herein wherein the PD-L1 is recombinant human PD-L1.

One aspect described herein provides a nucleic acid encoding a recombinant fusion protein, a vector comprising the nucleic acid, and a host cell comprising the vector. In one embodiment, the vector encodes a nucleic acid molecule linked to a signal peptide sequence.

Another aspect described herein provides a method of making a fusion protein comprising the extracellular domain of PD-1 and/or PD-L1 protein, said method comprising: (a) transfecting a host cell with a nucleic acid molecule encoding the fusion protein, wherein the nucleic acid molecule comprises a nucleotide sequence encoding a signal peptide, fused to either i) a nucleotide sequence encoding an Fc domain of a human or mouse IgG linked to a nucleotide sequence encoding the extracellular domain of PD-1 and/or PD-L1 peptide, at the N-terminus of said extracellular domain of PD-1 and/or PD-L1 peptide, or ii) a nucleotide sequence encoding the PD-1 and/or PD-L1 peptide linked to a nucleotide sequence encoding an Fc domain of a human or mouse or other mammalian IgG, at the N-terminus of said Fc domain, and (b) making the fusion protein by expressing the nucleic acid molecule of (a) in the host cell. In one embodiment, the extracellular domain is fused to the Fc domain via a linker. The linker may be SEQ ID NO: 4 or SEQ ID NO: 5. Another aspect describe herein provides a method of making a fusion protein comprising the extracellular domain of PD-1 and/or PD-L1 protein, said method comprising: (a) transfecting a host cell with a nucleic acid molecule encoding the fusion protein as described herein, and (b) making the fusion protein by expressing the nucleic acid molecule of (a) in the host cell.

For recombinant production of the fusion protein, a wide variety of expression vectors can be constructed based on common molecular cloning protocols. The vector components generally include, but are not limited to, one or more of the following: a signal sequence for the secretion of expressed proteins, one or more marker genes including the selection marker gene for the stable cell line screening in eukaryote cells, an origin of replication, an enhancer element, a promoter, a transcription termination sequence, a poly A signal, an insulator, etc.

Also provided herein is a composition comprising a fusion protein comprising PD-1 and/or PD-L1, or a fragment thereof, and an oligomerization domain. Further provided herein is a method of making a composition comprising a fusion protein comprising PD-1 and/or PD-L1 or a fragment thereof and an oligomerization domain as described herein. A kit comprising the fusion protein or the composition is also provided.

In addition, provided herein are methods for antibody biomonitoring using the fusion proteins as antigens. The fusion proteins described herein can serve as antigen(s) for therapeutic antibody biomonitoring. The antibody includes anti-PD-1 (such as Nivolumab and Pembrolizumab) and/or anti-PD-L1 antibodies (Atezolizumab and Avelumab).

One aspect described herein provides a method for diagnosing, monitoring or staging diseases mediated by PD-1 and/or PD-L1 comprising contacting a sample from a patient, having undergone at least one dose of immunotherapy, with a fusion protein disclosed herein.

One aspect described herein provides a method for determining the efficacy of therapeutic anti-PD-1 and/or PD-L1 antibodies comprising contacting a sample from a patient, having undergone at least one dose of immunotherapy, with a fusion protein disclosed herein.

Another aspect described herein includes a method of providing an immunotherapy to a patient comprising administering to the patient a therapeutic antibody and detecting the presence of anti-PD-1 and/or anti-PD-L1 therapeutic antibodies. It is envisioned that these methods can be used to monitor the efficacy of antibody-based therapy.

Another aspect described herein includes methods for detecting and/or monitoring diseases mediated by PD-1 and/or PD-L1 by measuring anti-PD-1 and/or anti-PD-L1 therapeutic antibodies. In some aspects the method comprises contacting a sample from a patient with a fusion protein described herein. In some aspects, the patient has undergone a course of immunotherapy with a therapeutic antibody.

In some aspects the present invention relates to a method of determining the amount of circulating levels of a biotherapeutic antibody selected from the group consisting of nivolumab, pembrolizumab and other anti-PD-1 therapies, comprising (i) obtaining a sample from a patient undergoing the antibody treatment, and (ii) contacting the sample with the fusion protein described herein.

In some aspects the present invention relates to a method of determining the amount of (free) circulating levels of a biotherapeutic antibody selected from the group consisting of atezolizumab, avelumab, and other anti PD-L1 therapies, comprising (i) obtaining a sample from a patient undergoing the antibody treatment, and (ii) contacting the sample with the fusion protein described herein.

The use of the word "a" or "an" when used in conjunction with the term "comprising" in the claims and/or the specification may mean "one," but it is also consistent with the meaning of "one or more," "at least one," and "one or more than one."

The foregoing has outlined rather broadly the features and technical advantages of the embodiments disclosed herein in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of various embodiments disclosed herein. It should also be realized by those skilled in the art that such equivalent constructions do not depart from the spirit and scope of the invention as set forth in the appended claims. The novel features which are believed to be characteristic of various embodiments disclosed herein, both as to their organization and method of operation, together with further objects and advantages will be better understood from the following description when considered in connection with the accompanying figures. It is to be expressly understood, however, that each of the figures is provided for the purpose of illustration and description only and is not intended as a definition of the limits of the disclosed embodiments.

BRIEF DESCRIPTION OF THE SEQUENCES

Figure 1:
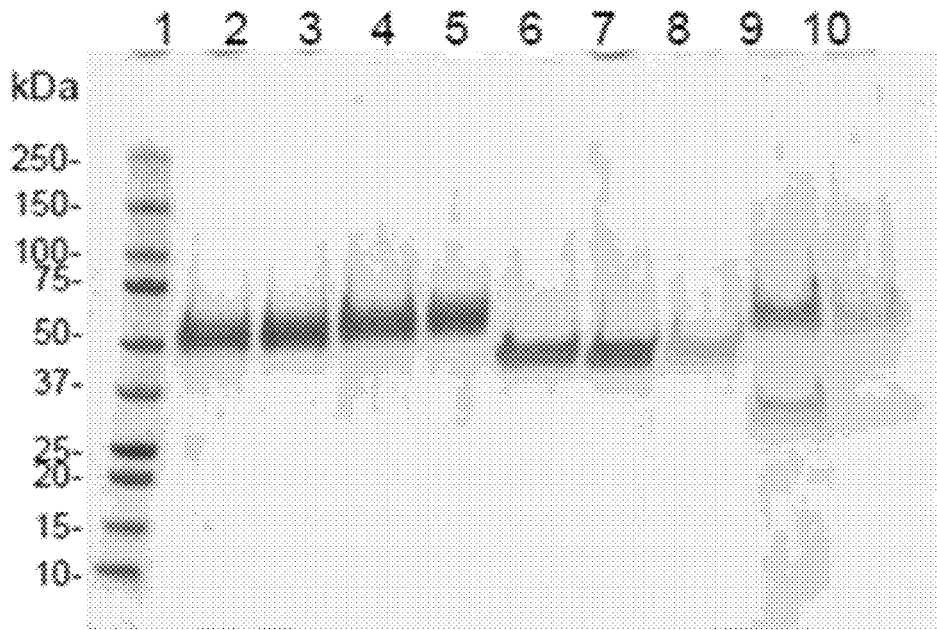
FIG. 1—Represents SDS-PAGE chromatography of various fusion proteins post expression and purification with a reducing 4-20% Tris-glycine TGX gel.

SEQ ID NO: 1 is the amino acid sequence of PD-1 (UniProt: Q15116).
SEQ ID NO: 2 is the amino acid sequence of PD-L1 (UniProt: Q9NZQ7)

SEQ ID NO: 3 is the amino acid sequence of Human IL2 signal peptide.

SEQ ID NO: 4 is the amino acid sequence of flexible Gly-Ser linker.

SEQ ID NO: 5 is the amino acid sequence of flexible Gly-Pro-Ser linker (Flex Pro Linker).

SEQ ID NO: 6 is the amino acid sequence of Murine IgG1 containing CH2 and CH3 domains only.

SEQ ID NO: 7 is the amino acid sequence of Murine IgG1 containing Fc region.

SEQ ID NO: 8 is the amino acid sequence of Murine IgG2A containing Fc region.

SEQ ID NO: 9 is the amino acid sequence of GCN4 trimer domain.

SEQ ID NO: 10 is the amino acid sequence of Clathrin trimer domain.

SEQ ID NO: 11 is the amino acid sequence of p53 tetramer domain.

SEQ ID NO: 12 is the amino acid sequence of PD-1 fragment.

SEQ ID NO: 13 is the amino acid sequence of PD-L1 fragment.

SEQ ID NO: 14 is the amino acid sequence of a PD-1 fusion protein (HuIL2SS-PD-1(GGGGS)2-Murine IgG1 (CH2, CH3 ONLY) 362 AA Flex Linker) according to one embodiment of the invention.

SEQ ID NO: 15 is the amino acid sequence of a PD-1 fusion protein (HuIL2SS-PD-1 (GGGPS)2-Murine IgG1 (CH2, CH3 ONLY) 362 AA Flex Pro Linker) according to another embodiment of the invention.

SEQ ID NO: 16 is the amino acid sequence of a PD-1 fusion protein (HuIL2SS-PD-1-murine IgG1 Fc 365 AA No hinge) according to yet another embodiment of the invention.

SEQ ID NO: 17 is the amino acid sequence of a PD-1 fusion protein (HuIL2SS-PD-1-murine IgG2A Fc 370 AA No hinge) according to yet another embodiment of the invention.

SEQ ID NO: 18 is the amino acid sequence of a PD-1 fusion protein (HuIL2SS-PD-1-GCN4 trimer domain) according to yet another embodiment of the invention.

SEQ ID NO: 19 is the amino acid sequence of a PD-1 fusion protein (HuIL2SS-PD-1-Clathrin trimer domain) according to yet another embodiment of the invention.

SEQ ID NO: 20 is the amino acid sequence of a PD-1 fusion protein (HuIL2SS-PD-1-p53 tetramer domain) according to yet another embodiment of the invention.

SEQ ID NO: 21 is the amino acid sequence of a PD-L1 fusion protein (HuIL2SS-PD-L1(GGGGS)2-Murine IgG1 (CH2, CH3 ONLY) 361 AA Flex linker) according to one embodiment of the invention.

SEQ ID NO: 22 is the amino acid sequence of a PD-L1 fusion protein (HuIL2SS-PD-L1(GGGPS)2-Murine IgG1 (CH2, CH3 ONLY) 361 AA flex pro linker) according to another embodiment of the invention.

SEQ ID NO: 23 is the amino acid sequence of a PD-L1 fusion protein (HuIL2SS-PD-L1-murine IgG1 Fc 364 AA no hinge) according to yet another embodiment of the invention.

SEQ ID NO: 24 is the amino acid sequence of a PD-L1 fusion protein (HuIL2SS-PD-L1-murine IgG2A Fc 370 AA No hinge) according to yet another embodiment of the invention.

SEQ ID NO: 25 is the amino acid sequence of a PD-L1 fusion protein (HuIL2SS-PD-L1-GCN4 trimer domain) according to yet another embodiment of the invention.

SEQ ID NO: 26 is the amino acid sequence of a PD-L1 fusion protein (HuIL2SS-PD-L1-Clathrin trimer domain) according to yet another embodiment of the invention.

SEQ ID NO: 27 is the amino acid sequence of a PD-L1 fusion protein (HuIL2SS-PD-L1-p53 tetramer domain) according to yet another embodiment of the invention.

SEQ ID NO: 28 is the amino acid sequence of Murine IgG2A containing CH2 and CH3 domains only.

SEQ ID NO: 29 is the amino acid sequence of a PD-1 fusion protein (HuIL2SS-PD-1(GGGGS)2-p53-Histag) according to one embodiment of the invention.

SEQ ID NO: 30 is the amino acid sequence of a PD-L1 fusion protein (HuIL2SS-PD-L1(GGGGS)2-p53-Histag) according to one embodiment of the invention.

SEQ ID NO: 31 is the amino acid sequence of a polyhistidine tag according to one embodiment of the invention.

DETAILED DESCRIPTION

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

The following terms, unless otherwise indicated, shall be understood to have the following meanings:

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "nucleic acid" refers to any materials comprised of DNA or RNA. Nucleic acids can be made synthetically or by living cells.

As used herein, the term "polynucleotide" refers to a polymeric chain of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

As used herein, the term "protein" refers to large biological molecules, or macromolecules, consisting of one or more chains of amino acid residues. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. However, proteins may be completely artificial or recombinant, i.e., not existing naturally in a biological system.

As used herein, the term "polypeptide" refers to both naturally-occurring and non-naturally-occurring proteins, and fragments, mutants, derivatives and analogs thereof. A polypeptide may be monomeric or polymeric. A polypeptide may comprise a number of different domains each of which has one or more distinct activities. A polypeptide may be a fusion protein, as described herein.

As used herein, the term "fusion protein" refers to proteins comprising two or more amino acid sequences that do not co-exist in naturally-occurring proteins. A fusion protein may comprise two or more amino acid sequences from the same or from different organisms. The two or more amino acid sequences of a fusion protein are typically in frame without stop codons between them and are typically translated from mRNA as part of the fusion protein.

As used herein, the term "antigen" refers to a biomolecule that binds specifically to the respective antibody. An antibody from the diverse repertoire binds a specific antigenic structure by means of its variable region interaction (CDR loops), an analogy being the fit between a lock and a key.

The term "variant," when used in the context of a polynucleotide sequence, may encompass a polynucleotide sequence related to a wild type gene. This definition may also include, for example, "allelic", "splice," "species," or "polymorphic" variants. A splice variant may have significant identity to a reference molecule, but will generally have a greater or lesser number of polynucleotides due to alternate splicing of exons during MRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The terms "antibody" or "immunoglobulin", as used herein, have the same meaning, and will be used equally in the present invention. The term "antibody" as used herein refers to immunoglobulin molecules and immunologically active portions of immunoglobulin molecules, i.e., molecules that contain an antigen binding site that immune specifically binds an antigen. As such, the term antibody encompasses not only whole antibody molecules, but also antibody fragments or derivatives. Antibody fragments include but are not limited to Fc, Fv, Fab, F(ab')$_2$, Fab', dsFv, scFv, sc(Fv)$_2$ and diabodies.

In natural antibodies, two heavy chains are linked to each other by disulfide bonds and each heavy chain is linked to a light chain by a disulfide bond. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). —Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

Many approved therapeutic antibodies have used the G1m17.1:Km3 heavy and light chain constant region allotypes (Jeffris and Lefranc 2009). Others use alternative G1 m3:Km3 allotypes. The role of allotype in rejection of therapeutic antibodies was not apparent at the outset of mAb therapy as differences in allotypy were not known to be as common as they are today. There is a clear link between the allotype of therapeutic mAbs and clearance. This is due to the interaction differences with the FcRn neonatal Fc receptor which function to keep some of the mAb sequestered within cellular compartments to be recycled back into the blood stream and not cleared rapidly (Ternant et al 2016). These difference in allotypy and the effects on cellular immune stimulation are becoming more known today (Webster et al 2016). While unlikely to generate immunogenicity they have a clear effect on half-life. Thus tests to measure the amount of circulating therapeutic antibody can reveal levels of drug and potential needs for dose escalation. Alternatively, some patients may require less drug to maintain an effective level in particular if the level of anti-PD-1 on the T cell surface maintains a high level. These antigens can be used to measure binding by any type of antibody (IgG1, IgG4, DARTs, BiTes etc) if used in conjunction with specific reagents or in competition assays familiar to those schooled in the art of Immunoassay.

Next generation combination therapy using multiple immune checkpoint inhibitor mAbs and other drugs also require effective means of monitoring levels. These types of combination treatments are not only more effective but are becoming common (Dempke et al 2017). Assays described herein will also be important to measure the anti-PD-1 or anti-PD-L1 components in these cases.

As used herein, "site-directed mutagenesis" refers to a process in which a mutation is created at a defined site in a DNA molecule. The defined site refers to sites chosen as based on the affinity of interaction. The DNA molecule for mutagenesis usually is a circular molecule known as a plasmid. In general, site-directed mutagenesis requires that the wild-type gene sequence be known. This technique is also known as "site-specific mutagenesis" or "oligonucleotide-directed mutagenesis". Consequently, "site-directed mutation" means mutations created at a defined site in a DNA molecule by technique of site-directed mutagenesis. In one embodiment, a mutant DNA sequence generated using site directed mutagenesis have more than 40%, more than 45%, more than 50%, more than 55%, more than 60%, more than 65%, more than 70%, more than 75%, more than 80%, more than 85%, more than 90%, more than 95%, or more than 98% homology with the wild-type sequence. Alternatively, mutant DNA may be generated in vivo using any known mutagenic procedure (e.g., radiation, nitrosoguanidine, etc.). The DNA construct sequences may be wild-type, mutant or modified. In addition, the sequences may be homologous or heterologous.

The terms "wild-type sequence" or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced binding affinity).

As used herein, the term "linker" refers to a polypeptide comprising of 1-30 amino acids, preferably 3-6 amino acids. The amino acids of the linker may be selected from the group consisting of leucine (Leu, L), isoleucine (Ile, I), alanine (Ala, A), glycine (Gly, G), valine (Val, V), proline (Pro, P), lysine (Lys, K), arginine (Arg, R), Serine (Ser, S), asparagine (Asn, N), and glutamine (Gin, Q), tryptophan (Trp, VV), methionine (Met, M) aspartic acid (Asp, D), cysteine (Cys, C), glutamic acid (Glu, E), histidine (His, H), phenylalanine (Phe, F), threonine (The, T), and tyrosine (Tyr, Y).

"Diagnostic" or "diagnosed" means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

The term "sample", as used herein, refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells.

The term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The term "prevention", as used herein, refers to preventing the disease or condition from occurring in a subject which has not yet been diagnosed as having it.

The terms "cancer", "hyperproliferative" and "neoplastic", as used herein, refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

One aspect described herein utilizes therapeutic antibodies to diagnose, monitor or stage diseases mediated by PD-1 and/or PD-L1 and efficacy of therapy. More particularly, methods of detecting and monitoring a therapeutic antibody, wherein a patient has undergone at least one course of immunotherapy, are disclosed. A variety of cancers or chronic infections can be monitored, staged or diagnosed according to the methods disclosed herein.

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm. Examples of non-hematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer Examples of chronic infections include, but are not limited to, viral, bacterial, parasitic or fungal infections such as chronic hepatitis, lung infections, lower respiratory tract infections, bronchitis, influenza, *pneumoniae* and sexually transmitted diseases. Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever. Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, *salmonellosis*, scarlet fever, shigellosis, syphilis, tetanus, trachoma, tularemia, typhoid fever, and urinary tract infections. Examples of parasitic infections include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis.

The methods disclosed herein can be utilized to determine a dosage of a therapeutic anti-PD-1 and/or anti-PD-L1 antibodies. Specifically, the method comprises testing a sample from a human, having undergone at least one course of immunotherapy, to measure the level of therapeutic anti-PD-1 and/or anti-PD-L1 antibodies, wherein depending on the level of the antibodies, further treatment with the antibodies can be adjusted.

In a further embodiment, the disclosure herein relates to a method for detecting the responsiveness of a patient to a therapeutic antibody treatment, wherein the therapeutic antibody is directed against PD-1 and/or PD-L1, the method comprising determining, in a sample from the patient, the presence or amount of inactive TNFalpha, said presence or amount being indicative of low or decreasing responsiveness of the patient to said treatment. In a preferred embodiment, the method also comprises a determination of the presence or amount of the therapeutic antibody and Anti-Drug Antibodies directed against said therapeutic antibody to obtain a patient profile, wherein the patient profile indicates the responsiveness to said treatment.

PD-1 and PD-L1

The present invention relates to fusion proteins comprising an extracellular domain of PD-1 (programmed cell death-1 protein) and an oligomerization domain, and/or to fusion proteins comprising an extracellular domain of PD-L1 (programmed cell death-ligand 1 protein) and an oligomerization domain.

The PD-1 and PD-L1 sequences may be variants of the native human sequences. As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. A polypeptide may have a characteristic sequence element comprised of a plurality of amino acids having designated positions relative to one another in linear or three-dimensional space and/or contributing to a particular biological function. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

In one embodiment described herein, the fusion protein comprises the predicted extracellular domain of PD-1 protein (SEQ ID NO: 1) or a fragment thereof. In one aspect, the extracellular domain of PD-1 protein comprises SEQ ID NO: 12 or a fragment thereof. In another aspect, the extracellular domain of PD-1 may have about 70%, 75%, 80%, 85%, 90%, 91%, 92%, 93%, 94%, 95%, 96%, 97%, 98%, 99% or more homology to the polypeptide sequence consisting of the amino acids at positions 21 to 170 of SEQ ID NO: 1.

The extracellular domain of PD-1 comprises a polypeptide comprising residues 1 to 171 of SEQ ID NO: 1, a polypeptide comprising residues 1 to 170 of SEQ ID NO: 1, a polypeptide comprising residues 1 to 145 of SEQ ID NO: 1, a polypeptide comprising residues 21 to 171 of SEQ ID NO: 1, a polypeptide comprising residues 21 to 170 of SEQ ID NO: 1, a polypeptide comprising residues 21 to 145 of SEQ NO: 1, a polypeptide comprising residues 33 to 171 of SEQ ID NO: 1, a polypeptide comprising residues 33 to 170 of SEQ ID NO: 1, a polypeptide comprising residues 33 to 145 of SEQ ID NO: 1, a polypeptide comprising residues 35 to 171 of SEQ ID NO: 1, a polypeptide comprising residues 35 to 170 of SEQ ID NO: 1, and a polypeptide comprising residues 35 to 145 of SEQ ID NO: 1. In one embodiment, the extracellular domain of PD-1 may have about 70%, 75%, 80%, 85%, 90%, 91%, 92%, 93%, 94%, 95%, 96%, 97%, 98%, 99% or more homology to a polypeptide comprising residues 1 to 171 of SEQ ID NO: 1, a polypeptide comprising residues 1 to 170 of SEQ ID NO: 1, a polypeptide comprising residues 1 to 145 of SEQ ID NO: 1, a polypeptide comprising residues 21 to 171 of SEQ ID NO: 1, a polypeptide comprising residues 21 to 170 of SEQ ID NO: 1, a polypeptide comprising residues 21 to 145 of SEQ NO: 1, a polypeptide comprising residues 33 to 171 of SEQ ID NO: 1, a polypeptide comprising residues 33 to 170 of SEQ ID NO: 1, a polypeptide comprising residues 33 to 145 of SEQ ID NO: 1, a polypeptide comprising residues 35 to 171 of SEQ ID NO: 1, a polypeptide comprising residues 35 to 170 of SEQ ID NO: 1, and a polypeptide comprising residues 35 to 145 of SEQ ID NO: 1. In yet another embodiment, the extracellular domain of PD-1 comprises the amino acid sequence set forth in SEQ ID NO: 12. In another embodiment, the extracellular domain of PD-1 may have about 70%, 75%, 80%, 85%, 90%, 91%, 92%, 93%, 94%, 95%, 96%, 97%, 98%, 99% or more homology to the amino acid sequence set forth in SEQ ID NO: 12.

In another embodiment described herein, the fusion protein comprises the extracellular domain of PD-L1 protein (SEQ ID NO: 2) or a fragment thereof. In another embodiment, the extracellular domain of PD-L1 protein comprises SEQ ID NO: 13 or a fragment thereof. In addition, the extracellular domain of PD-L1 may have about 70%, 75%, 80%, 85%, 90%, 91%, 92%, 93%, 94%, 95%, 96%, 97%, 98%, 99% or more homology to the polypeptide sequence consisting of the amino acids at positions 19 to 238 of SEQ ID NO: 2.

The extracellular domain of PD-L1 may be a polypeptide comprising residues 1 to 240 of SEQ ID NO: 2, a polypeptide comprising residues 1 to 239 of SEQ ID NO: 2, a polypeptide comprising residues 1 to 238 of SEQ ID NO: 2, a polypeptide comprising residues 19 to 240 of SEQ ID NO: 2, a polypeptide comprising residues 19 to 239 of SEQ ID NO: 2, a polypeptide comprising residues 19 to 238 of SEQ NO: 2, a polypeptide comprising residues 18 to 239 of SEQ ID NO: 2, a polypeptide comprising residues 18 to 238 of SEQ ID NO: 2, a polypeptide comprising residues 18 to 225 of SEQ ID NO: 2, a polypeptide comprising residues 18 to 134 of SEQ ID NO: 2, a polypeptide comprising residues 18 to 127 of SEQ ID NO: 2, a polypeptide comprising residues 19 to 239 of SEQ ID NO: 2, a polypeptide comprising residues 19 to 238 of SEQ ID NO: 2, a polypeptide comprising residues 19 to 225 of SEQ ID NO: 2, a polypeptide comprising residues 19 to 134 of SEQ ID NO: 2, a polypeptide comprising residues 19 to 127 of SEQ ID NO: 2, a polypeptide comprising residues 133 to 225 of SEQ ID NO: 2, a polypeptide comprising residues 133 to 238 of SEQ ID NO: 2, and a polypeptide comprising residues 133 to 239 of SEQ ID NO: 2. In one embodiment, the extracellular domain of PD-L1 may have about 70%, 75%, 80%, 85%, 90%, 91%, 92%, 93%, 94%, 95%, 96%, 97%, 98%, 99% or more homology to a polypeptide comprising residues 1 to 240 of SEQ ID NO: 2, a polypeptide comprising residues 1 to 239 of SEQ ID NO: 2, a polypeptide comprising residues 1 to 238 of SEQ ID NO: 2, a polypeptide comprising residues 19 to 240 of SEQ ID NO: 2, a polypeptide comprising residues 19 to 239 of SEQ ID NO: 2, a polypeptide comprising residues 19 to 238 of SEQ NO: 2, a polypeptide comprising residues 18 to 239 of SEQ ID NO: 2, a polypeptide comprising residues 18 to 238 of SEQ ID NO: 2, a polypeptide comprising residues 18 to 225 of SEQ ID NO: 2, a polypeptide comprising residues 18 to 134 of SEQ ID NO: 2, a polypeptide comprising residues 18 to 127 of SEQ ID NO: 2, a polypeptide comprising residues 19 to 239 of SEQ ID NO: 2, a polypeptide comprising residues 19 to 238 of SEQ ID NO: 2, a polypeptide comprising residues 19 to 225 of SEQ ID NO: 2, a polypeptide comprising residues 19 to 134 of SEQ ID NO: 2, a polypeptide comprising residues 19 to 127 of SEQ ID NO: 2, a polypeptide comprising residues 133 to 225 of SEQ ID NO: 2, a polypeptide comprising residues 133 to 238 of SEQ ID NO: 2, and a polypeptide comprising residues 133 to 239 of SEQ ID NO: 2. In yet another embodiment, the extracellular domain of PD-L1 comprises the amino acid sequence set forth in SEQ ID NO: 13. In another embodiment, the extracellular domain of PD-L1 may have about 70%, 75%, 80%, 85%, 90%, 91%, 92%, 93%, 94%, 95%, 96%, 97%, 98%, 99% or more homology to the amino acid sequence set forth in SEQ ID NO: 13.

In addition, certain residues may be modified, by site-directed-mutagenesis, for improved higher affinity interaction between known mAbs and their target. In some embodiments, the modification constitutes substitution of 10, 9, 8, 7, 6, 5, 4, 3, 2, or 1 residue as compared with a parent. Often, modification utilizing site-directed-mutagenesis has a very small number (e.g., fewer than 5, 4, 3, 2, or 1) of substituted functional residues (i.e., residues that participate in a binding affinity). Furthermore, modification utilizing site-directed-mutagenesis typically has not more than 5, 4, 3, 2, or 1 additions or deletions, and often has no additions or deletions, as compared with the parent. Moreover, any additions, deletions or substitutions are typically fewer than about 50 residues, about 45 residues, about 40 residues, about 35 residues, about 30 residues, about 25 residues, about 20 residues, about 19 residues, about 18 residues, about 17 residues, about 16 residues, about 15 residues, about 14 residues, about 13 residues, about 12 residues, about 11 residues, about 10 residues, about 9 residues, about 8 residues, about 7 residues, about 6 residues, and commonly are fewer than about 5 residues, about 4 residues, about 3 residues, or about 2 residues. In some embodiments, the parent or reference polypeptide is one found in nature.

In one embodiment, one or more amino acid residue(s) within PD-1 critical for interaction with an anti-PD-1 antibody is/are modified for improved higher affinity interaction between antibodies and their target. In some embodiment, the one or more amino acid residue(s) modified within PD-1 are involved in hydrogen bonding. In another embodiment, the one or more amino acid residue(s) modified within PD-1 are involved in forming salt bridges. In yet another embodiment, the one or more amino acid residue(s) modified within PD-1 are involved in water mediated interactions. In yet another embodiment, the one or more amino acid residue(s) modified within PD-1 are involved in van der Waals interactions.

In one embodiment, one or more amino acid residue(s) within PD-1 critical for interaction with the Pembrolizumab mAb is/are modified. In a related embodiment, the one or more amino acid residue(s) modified within PD-1 can be selected from the group consisting of $_{PD\text{-}1}$N66, $_{PD\text{-}1}$T76, $_{PD\text{-}1}$K78, $_{PD\text{-}1}$S87, $_{PD\text{-}1}$K131 $_{PD\text{-}1}$F63, $_{PD\text{-}1}$E84, $_{PD\text{-}1}$S87, $_{PD\text{-}1}$G90 and $_{PD\text{-}1}$A132. In another related embodiment, the amino acid residue modified within PD-1 is $_{PD\text{-}1}$D85. In yet another embodiment, related embodiment, the one or more amino acid residue(s) modified within PD-1 can be selected from the group consisting of $_{PD\text{-}1}$K78, $_{PD\text{-}1}$S87 and $_{PD\text{-}1}$D85. In yet another embodiment, related embodiment, the one or more amino acid residue(s) modified within PD-1 can be selected from the group consisting of $_{PD\text{-}1}$V64, $_{PD\text{-}1}$Y68, $_{PD\text{-}1}$Q75, $_{PD\text{-}1}$D77, $_{PD\text{-}1}$A81, $_{PD\text{-}1}$F82, $_{PD\text{-}1}$P83, $_{PD\text{-}1}$R86, $_{PD\text{-}1}$Q88, $_{PD\text{-}1}$P89, $_{PD\text{-}1}$G90, $_{PD\text{-}1}$I126, $_{PD\text{-}1}$I128, $_{PD\text{-}1}$A129, and $_{PD\text{-}1}$I134. In yet another embodiment, related embodiment, the one or more amino acid residue(s) modified within PD-1 can be selected from the group consisting of $_{PD\text{-}1}$N66, $_{PD\text{-}1}$T76, $_{PD\text{-}1}$K78, $_{PD\text{-}1}$S87, $_{PD\text{-}1}$K131 $_{PD\text{-}1}$F63, $_{PD\text{-}1}$E84, $_{PD\text{-}1}$S87, $_{PD\text{-}1}$G90, $_{PD\text{-}1}$A132, $_{PD\text{-}1}$D85, $_{PD\text{-}1}$K78, $_{PD\text{-}1}$S87 and $_{PD\text{-}1}$D85, $_{PD\text{-}1}$V64, $_{PD\text{-}1}$Y68, $_{PD\text{-}1}$Q75, $_{PD\text{-}1}$D77, $_{PD\text{-}1}$A81, $_{PD\text{-}1}$F82, $_{PD\text{-}1}$P83, $_{PD\text{-}1}$R86, $_{PD\text{-}1}$Q88, $_{PD\text{-}1}$P89, $_{PD\text{-}1}$G90, $_{PD\text{-}1}$I126, $_{PD\text{-}1}$I128, $_{PD\text{-}1}$A129, and $_{PD\text{-}1}$I134.

In one embodiment, one or more amino acid residue(s) within PD-1 critical for interaction with the Nivolumab mAb is/are modified. In a related embodiment, the one or more amino acid residue(s) modified within PD-1 can be selected from the group consisting of $_{PD\text{-}1}$P28, $_{PD\text{-}1}$I128, $_{PD\text{-}1}$A129, $_{PD\text{-}1}$P130, $_{PD\text{-}1}$A132, $_{PD\text{-}1}$D29, $_{PD\text{-}1}$R30, $_{PD\text{-}1}$S60 and $_{PD\text{-}1}$K131. In another related embodiment, the one or more amino acid residue(s) modified within PD-1 can be selected from the group consisting of $_{PD\text{-}1}$S27, $_{PD\text{-}1}$P28, $_{PD\text{-}1}$P31, $_{PD\text{-}1}$E61, $_{PD\text{-}1}$A129, $_{PD\text{-}1}$P130, $_{PD\text{-}1}$K131, $_{PD\text{-}1}$A132 and $_{PD\text{-}1}$Q133.

In one embodiment, the one or more amino acid residue(s) modified within PD-1 are involved in hydrogen bonding or van der waals interactions between either Nivolumab or Pembrolizumab and PD-1. In a specific embodiment, the one or more amino acid residue(s) modified within PD-1 can be selected from the group consisting of $_{PD\text{-}1}$L128, $_{PD\text{-}1}$A129, $_{PD\text{-}1}$A130, $_{PD\text{-}1}$K131, and $_{PD\text{-}1}$A132.

In one embodiment, one or more amino acid residue(s) within the Pembrolizumab mAb critical for interaction with PD-1 is/are modified. In some embodiments, the one or more amino acid residue(s) within the Pembrolizumab mAb that are modified include residues within the heavy chain CDR1 (HCDR1). In some embodiments, the one or more amino acid residue(s) modified within the HCDR1 Pembrolizumab mAb can be selected from the group consisting of $_{heavy}$T30, $_{heavy}$Y33, and $_{heavy}$Y35. In some embodiments, the one or more amino acid residue(s) within the Pembrolizumab mAb that are modified include residues within the heavy chain CDR2 (HCDR2). In some embodiments, the one or more amino acid residue(s) modified within the HCDR2 Pembrolizumab mAb can be selected from the group consisting of $_{heavy}$N52, $_{heavy}$S54, $_{heavy}$N55, $_{heavy}$G57, $_{heavy}$T58, and $_{heavy}$N59. In some embodiments, the one or more amino acid residue(s) within the Pembrolizumab mAb that are modified include residues within the heavy chain CDR3 (HCDR3). In some embodiments, the one or more amino acid residue(s) modified within the HCDR3 Pembrolizumab mAb can be selected from the group consisting of $_{heavy}$R99, $_{heavy}$Y101, $_{heavy}$R102, $_{heavy}$F103, $_{heavy}$D104, $_{heavy}$M105, and $_{heavy}$D108. In some embodiments, the one or more amino acid residue(s) within the Pembrolizumab mAb that are modified include residues within the light chain CDR1 (LCDR1). In some embodiments, the one or more amino acid residue(s) modified within the LCDR1 Pembrolizumab mAb can be selected from the group consisting of $_{light}$T31, $_{light}$S32, $_{light}$Y34, and $_{light}$Y36. In some embodiments, the one or more amino acid residue(s) within the Pembrolizumab mAb that are modified include residues within the light chain CDR2 (LCDR2). In some embodiments, the one or more amino acid residue(s) modified within the LCDR2 Pembrolizumab mAb can be selected from the group consisting of $_{light}$Y53, $_{light}$L54, $_{light}$Y57, and $_{light}$E59. In some embodiments, the one or more amino acid residue(s) within the Pembrolizumab mAb that are modified include residues within the light chain CDR3 (LCDR3). In some embodiments, the one or more amino acid residue(s) modified within the LCDR3 Pembrolizumab mAb can be selected from the group consisting of $_{light}$S95, $_{light}$R96, $_{light}$D97, $_{light}$L98 and $_{light}$L100.

In one embodiment, one or more amino acid residue(s) within the Nivolumab mAb that critical for interaction with PD-1 is/are modified. In some embodiments, the one or more amino acid residue(s) within the Nivolumab mAb that are modified include residues within the heavy chain CDR1 (HCDR1). In some embodiments, the one or more amino acid residue(s) modified within the HCDR1 Pembrolizumab mAb can be selected from the group consisting of $_{heavy}$G26, $_{heavy}$I27, $_{heavy}$N31 and $_{heavy}$G33. In some embodiments, the one or more amino acid residue(s) within the Nivolumab mAb that are modified include residues within the heavy chain CDR2 (HCDR2). In some embodiments, the one or more amino acid residue(s) modified within the HCDR2 Pembrolizumab mAb can be selected from the group consisting of $_{heavy}$V50, $_{heavy}$W52 and $_{heavy}$Y53. In some embodiments, the one or more amino acid residue(s) within the Nivolumab mAb that are modified include residues within the heavy chain CDR3 (HCDR3). In some embodiments, the one or more amino acid residue(s) modified within the HCDR3 Pembrolizumab mAb can be selected from the group consisting of $_{heavy}$N99, $_{heavy}$D100, $_{heavy}$D101 and $_{heavy}$Y102. In some embodiments, the one or more amino acid residue(s) within the Nivolumab mAb that are modified include residues within the light chain CDR1 (LCDR1). In some embodiments, the one or more amino acid residue(s) within the Nivolumab mAb that are modified include residues within the light chain CDR2 (LCDR2). In some embodiments, the one or more amino acid residue(s) modified within the LCDR2 Pembrolizumab mAb can be selected from the group consisting of $_{light}$L46, $_{light}$A55 and $_{light}$T56. In some embodiments, the one or more amino acid residue(s) within the Nivolumab mAb that are modified include residues within the light chain CDR3 (LCDR3). In some embodiments, the amino acid residue modified within the LCDR3 Pembrolizumab mAb is $_{light}$S91.

In another embodiment, one or more amino acid residue(s) within PD-L1 critical for interaction with an anti-PD-L1 antibody is/are modified for improved higher affinity interaction between antibodies and their target. In some embodiment, the one or more amino acid residue(s) modified within PD-L1 are involved in hydrogen bonding. In another embodiment, the one or more amino acid residue(s) modified within PD-L1 are involved in forming salt bridges. In yet another embodiment, the one or more amino acid residue(s) modified within PD-L1 are involved in water mediated interactions. In yet another embodiment, the one or more amino acid residue(s) modified within PD-L1 are involved in van der Waals interactions.

Oligomerization Domains

The present invention discloses fusion proteins comprising an extracellular domain of PD-1 (programmed cell death-1 protein) or an extracellular domain of PD-L1 (programmed cell death-ligand 1 protein) and an oligomerization domain. The oligomerization domain described herein may comprise a domain selected from the group consisting of a Fc domain, a Clathrin trimerization domain, a GCN4 trimerization domain, a p53 tetramerization domain, and pentameric domains or even a hingeless monomeric Fc domain creating novel proteins. In some embodiments, the oligomerization domain lacks the oligomerization region and the fusion protein is a monomer. In some embodiments, the oligomerization domain is a hingeless monomeric Fc domain and the fusion protein is a monomer. The oligomerization domain may comprise virus like particles as a structure for exposure of the antigen or antibody variable domains. While these oligomerization domains are known by those expert in the art, they have not been used to create novel proteins for diagnostics.

In some aspects, the oligomerization domain may comprise an amino acid sequence selected from the group consisting of an Fc domain, a fragment of an Fc domain, and a variant of an Fc domain. In one embodiment, the fusion protein described herein can be part of a higher order structure, such as a protein or multimeric complex. In some embodiments, the PD-1 and/or PD-L1 protein is fused to the Fc domain, or fragment thereof, via one or more peptide linkers. In one embodiment, the PD-1 and/or PD-L1 protein is fused to the C-terminus of said Fc domain, or fragment thereof. In another embodiment, the PD-1 and/or PD-L1 protein is fused to the N-terminus of said Fc domain, or fragment thereof.

In some embodiments, the oligomerization domain comprises an amino acid sequence selected from the group consisting of SEQ ID NO: 6, SEQ ID NO: 7, SEQ ID NO: 8, SEQ ID NO: 9, SEQ ID NO: 10, SEQ ID NO: 11, or SEQ ID NO: 28.

In one embodiment, the oligomerization domain is selected from the group consisting of the amino acid sequence set forth in SEQ ID NO: 9 (GCN4 trimer domain), the amino acid sequence set forth in SEQ ID NO: 10 (clathrin trimer domain), and the amino acid sequence set forth in SEQ ID NO: 11 (p53 tetramer domain). In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 9 (GCN4 trimer domain). In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 10(clathrin trimer domain). In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 11 (p53 tetramer domain).

In one embodiment, the Fc domain comprises an immunoglobulin CH2 domain or an immunoglobulin CH3 domain. In another embodiment, the Fc domain comprises an immunoglobulin CH2 and CH3 domain. In some embodiments, the Fc domain is selected from the group consisting of IgG1 CH2 and CH3 domain, IgG4 CH2 and CH3 domain, IgG1 CH2 and an IgG4 CH3 domain, and IgG4 CH2 and an IgG1 CH3 domain. In some embodiments, the Fc domain may be of mouse or human. In some embodiments, the Fc domain may be of mouse IgG1 or IgG2A. In other embodiments, the Fc domain comprises an IgG hinge domain.

In one embodiment, the Fc domain is selected from the group consisting of the amino acid sequence set forth in SEQ ID NO: 6 (murine IgG1, CH2 and CH3), the amino acid sequence set forth in SEQ ID NO: 7 (murine IgG1 Fc), the amino acid sequence set forth in SEQ ID NO: 8 (murine IgG2A Fc), and the amino acid sequence set forth in SEQ ID NO: 28 (murine IgG2A, CH2 and CH3). In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 6. In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 7. In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 8. In some embodiments, the Fc domain may have about 70%, 75%, 80%, 85%, 90%, 91%, 92%, 93%, 94%, 95%, 96%, 97%, 98%, 99% or more homology to the amino acid sequence set forth in SEQ ID NO: 28.

As used herein, the term Ig "hinge" region refers to a polypeptide comprising an amino acid sequence that shares sequence identity, or similarity, with a portion of a naturally-occurring Ig hinge region sequence, which includes the cysteine residues at which the disulfide bonds link the two heavy chains of the immunoglobulin. Sequence similarity of the hinge region linkers described herein with naturally-occurring immunoglobulin hinge region amino acid sequences can range from at least 50% to about 75-80%, and typically greater than about 90%.

In some embodiments, the murine IgG1 Fc domain of the fusion protein of the present application comprises a hinge. In some embodiments, the murine IgG1 Fc domain of the fusion protein of the present application lacks a hinge. Exemplary amino acid sequence of murine IgG1 Fc domains are SEQ ID NO:6 (without hinge) and SEQ ID NO:7 (with hinge).

In some embodiments, the murine IgG2A Fc domain of the fusion protein of the present application comprises a hinge. In some embodiments, the murine IgG2A Fc domain of the fusion protein of the present application lacks a hinge.

Exemplary amino acid sequence of murine IgG2A Fc domains are SEQ ID NO:28 (without hinge) and SEQ ID NO:8 (with hinge).

Linkers

In some embodiments, the PD-1 and/or PD-L1 protein is fused to the oligomerization domain, or fragment thereof, via one or more peptide linkers. In one embodiment, the PD-1 and/or PD-L1 protein is fused to the C-terminus of said oligomerization domain, or fragment thereof, via one or more peptide linkers. In another embodiment, the PD-1 and/or PD-L1 protein is fused to the N-terminus of said oligomerization domain, or fragment thereof, via one or more peptide linkers.

In some embodiments, a peptide linker may consist of a sequence of consecutive amino acids that typically include at least one glycine, and at least one serine. A peptide linker may also consist of a sequence of consecutive amino acids that typically include at least one glycine, at least one proline and at least one serine. Exemplary flexible linkers and flexible pro linkers include the amino acid sequences set forth in SEQ ID NO:4 (GGGS) or SEQ ID NO:5 (GGGPS), although the precise amino acid sequence of an peptide linker is not particularly limiting. In some embodiments, the PD-1 and/or PD-L1 protein is fused to the oligomerization domain, or fragment thereof, via two or more different peptide linkers. In some embodiments the PD-1 and/or PD-L1 protein is fused to the oligomerization domain, or fragment thereof, via two or more identical peptide linkers A peptide linker, as described herein, is typically not found in nature, although some naturally-occurring amino acid sequences may serve as suitable linkers or may be used to design suitable linkers. A linker may include about 1 to 30 amino acids, such as about 2 to 25, about 3 to 20, about 4 to 16, or about 1, 2, 3, 4, 5, 6, 7, 8, 9, 10, 11, 12, 13, 14, 15, 16, 17, 18, 19, or 20 amino acids.

Signal Peptide Sequences

Fusion proteins disclosed herein typically comprise a signal peptide sequence (or "signal sequence" to favor translocation of the protein across the cell membrane of an expression vector, such as a mammalian cell, especially a human cell. A polypeptide may nevertheless lack a signal peptide sequence, for example, if the fusion protein disclosed herein typically comprise a signal peptide sequence to favor translocation of the polypeptide across the cell membrane of an expression vector, such as a mammalian cell, especially a human cell. A fusion protein may nevertheless lack a signal peptide sequence. Synthetically-produced polypeptides may similarly lack a signal peptide sequence.

A signal peptide sequence is typically included at the N-terminus of a fusion protein. A signal peptide sequence is preferably sufficient to translocate the protein outside of the cell surface membrane of a eukaryotic cell (e.g., a mammalian cell, such as a human cell) following the translation of the protein in the eukaryotic cell, although other sequence motifs of a fusion protein may also aid translocation.

An exemplary signal peptide sequence has the amino acid sequence set forth in SEQ ID NO:3 (MYRMQLLSCIALSLALVTNS), which is the human interleukin-2 signal peptide sequence. This well-characterized sequence is capable of translocating protein out of both human cells and other mammalian cells.

Affinity Tags

A fusion protein may optionally include an affinity tag. Affinity tags are useful for purification, and they may also be useful in assays that utilize a fusion protein. Exemplary affinity tags include polyhistidine, chitin binding protein, maltose binding protein, Strep-tag, glutathione-S-transferase, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, SpyTag, SnoopTag, biotin carboxyl carrier protein, green fluorescent protein-tag, HaloTag, Nus-tag, and thioredoxin-tag, although the choice of affinity tag is not particularly limiting. A fusion protein may nevertheless lack an affinity tag, for example, if the affinity tag is removed after use or if the fusion protein is purified using a strategy that does not require an affinity tag. An exemplary affinity tag is polyhistidine, which typically includes an amino acid sequence comprising seven consecutive histidines (SEQ ID NO:31). Another exemplary affinity tag is a polyhistidine tag comprising between 4 and 10 consecutive histidines.

Fusion Proteins

The fusion proteins featured in the embodiments described herein may comprise an extracellular domain of PD-1 (programmed cell death-1 protein) or an extracellular domain of PD-L1 (programmed cell death-ligand 1 protein) and an oligomerization domain, wherein the oligomerization domain is selected from the group consisting of a murine IgG1 Fc domain, a murine IgG2A Fc domain, a GCN4 trimer domain, a clathrin trimer domain, and a p53 tetramer domain, or a fragment thereof.

A fusion protein of the sort disclosed herein may have the amino acid sequence set forth in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, or SEQ ID NO:30. A fusion protein may have an amino acid sequence that has at least about 85%, 86%, 87%, 88%, 89%, 90%, 91%, 92%, 93%, 94%, 95%, 96%, 97%, 98%, 99%, or 99.5% sequence identity with the amino acid sequence set forth in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, or SEQ ID NO:30.

Nucleic Acids, Cloning Cells, and Expression Cells

Embodiments described herein also include a nucleic acid comprising a nucleotide sequence encoding a fusion protein described herein. The nucleic acid may be DNA or RNA. DNA comprising a nucleotide sequence encoding a fusion protein described herein typically comprises a promoter that is operably-linked to the nucleotide sequence. The promoter is preferably capable of driving constitutive or inducible expression of the nucleotide sequence in an expression cell of interest. The precise nucleotide sequence of the nucleic acid is not particularly limiting so long as the nucleotide sequence encodes a fusion protein described herein. Codons may be selected, for example, to match the codon bias of an expression cell of interest (e.g., a mammalian cell such as a human cell) and/or for convenience during cloning. DNA may be a plasmid, for example, which may comprise an origin of replication (e.g., for replication of the plasmid in a prokaryotic cell).

Various aspects of the present invention also relate to a cell comprising a nucleic acid comprising a nucleotide sequence that encodes a fusion protein as described herein. The cell may be an expression cell or a cloning cell. Nucleic acids are typically cloned in *E. coli*, although other cloning cells may be used. If the cell is an expression cell, the nucleic acid is optionally a nucleic acid of a chromosome, i.e., wherein the nucleotide sequence is integrated into the chromosome, although then nucleic acid may be present in an expression cell, for example, as extrachromosomal DNA.

Various aspects of the present invention include a cell comprising a nucleic acid comprising a sequence that encodes a fusion protein as described herein. The cell is typically an expression cell. The nature of the expression cell is not particularly limiting. Mammalian expression cells may allow for favorable folding, post-translational modifications, and/or secretion of a fusion protein or oligomeric fusion protein, although other eukaryotic cells or prokaryotic cells may be used as expression cells. Exemplary expression cells include CHO, BHK, NS0, Sp2/0, COS, C127, HEK, HT-1080, PER.C6, HeLa, and Jurkat cells.

Another aspect of the present invention herein provides a method of making a fusion protein comprising an extracellular domain of PD-1 (programmed cell death-1 protein) and/or an extracellular domain of PD-L1 (programmed cell death-ligand 1 protein), and an oligomerization domain comprising the steps of:
  a) transfecting a host cell with a nucleic acid molecule encoding the fusion protein according to the present invention,
  b) making the fusion protein by expressing the nucleic acid molecule of ( ) in the host cell.

Immunoassays and Reagents

Immunoassays are Usually Used to Measure Cell Surface Antigens or to Measure Antibodies in a Sample. Typically, immunofluorescence using flow cytometry is the immunoassay of choice. However, other immunoassays may be used, for example enzyme linked immunosorbent assays (ELISA). This technique is based upon the special properties of antigen-antibody interactions with simple phase separations to produce powerful assays for detecting biological molecules.

The methodology and instrumentation for the ELISA is simpler than that for immunofluorescence. Yet further, the ELISA and immunofluorescence assays are completely different assays. ELISA assays measure the protein (antigen) or antibody in the plasma/serum, which reflects the entire body. On the contrary, surface immunofluorescent assays specifically measure an antigen on the surface of individual cells and do not provide information on the amount of cells in the body. Thus, there are advantages in developing an ELISA assay to provide a measurement of the entire body.

One well-known and highly specific ELISA is a sandwich ELISA. In this assay, the antibody is bound to the solid phase or support, which is then contacted with the sample being tested to extract the antigen from the sample by formation of a binary solid phase antibody:antigen complex. After a suitable incubation period, the solid support is washed to remove the residue of the fluid sample and then contacted with a solution containing a known quantity of labeled antibody.

Some embodiments of the present invention are related to immunoassays for assaying a composition containing anti-PD-1 and/or anti-PD-L1 antibodies. Other embodiments relate to immunoassays for assaying a composition containing PD-1 and/or PD-L1 antigens.

Exemplary immunoassays according to the present invention are, for example, ELISA assays (Enzyme-Linked Immunosorbent Assay), which uses either colorimetric, fluorescent or chemiluminescent detection. Other exemplary immunoassays according to the present invention are well known by the skilled person, e.g. ELISA Using Slope Correction, RIA (radioimmunoassay), competitive EIA (competitive enzyme immunoassay), DAS-ELISA (double antibody sandwich-ELISA), bridging-ELISA, techniques based on the use of protein or antibody microarrays (including liquid bead-based arrays like those based on Luminex technology), technologies based on discrete microparticles, assays based on the precipitation of colloidal gold or other visible microparticles or fluorescent particles like lateral or vertical flow tests based on immunochromatography typically used for rapid testing and Point of Care applications using either visual (by eye) interpretation or a reader like a smartphone or a portable reader or a benchtop reader, affinity chromatography techniques, Homogeneous Mobility Shift Assays (HMSA), ligand binding assays, lectin binding assays, biosensors, etc.

It is known that the circulating anti-PD-1 antibodies have a similar half-life to other IgG4 antibodies (Farolfi et al 2016). Also, the PD-1 antibodies coat circulating T cells and effectively remove themselves from circulation (are no longer freely circulating in plasma). This causes a relatively rapid decline in circulating anti-PD-1 (nivolumab) levels in humans. The relationship between circulating levels, T-cell resident levels and outcome are not clear and thus an assay which can shed light on this is valuable. However, it is known that anti-PD-1 (Nivolumab) remains resident on circulating T cells for an extended period with an occupancy level of 60-80% depending upon the initial dose at 0.3 to 10 mg/kg (Brahmer et al 2010). In this function anti-PD-1 act as an antagonist of PD-1 preventing ligand binding to PD-L1 on tumors and the subsequent shut down of the immune response. It will be important to correlate dosing, T cell occupancy and measurable circulating anti-PD-1 or anti PD-L1 with outcomes. It is, therefore, an objective of the present disclosure to provide methods for detecting and/or monitoring anti-PD-1 and/or anti-PD-L1 antibodies.

Specifically, anti-PD-1 and/or anti-PD-L1 therapeutic antibodies, antibody:antigen complexes and/or antibodies that are directed at PD-1 and/or PD-L1 may be detected or monitored by using a modified sandwich ELISA technique or other immunoassay technique known to those familiar in the art.

In a particular embodiment, the concentration of the anti-PD-1 or anti-PD-L1 biological drugs is measured by ELISA, similarly that it is shown in the examples of the present invention.

The fusion proteins described herein may also be used to prevent or compete for binding of antibody to the same antigens on the surface of T cells or upon tumor cells.

In one aspect, anti-PD-1 and/or anti-PD-L1 therapeutic antibodies are measured in a patient that has undergone at least one dose of immunotherapy with a therapeutic antibody. The therapeutic antibody may include, but is not limited to anti-PD-1 or anti-PD-L1 therapeutic antibodies. The antibody:antigen complex is measured by ELISA techniques or other immunoassays and provides a determination of the circulating level of the therapeutic antibody. The interpretation of this result and the changes in treatment are then determined by an oncologist familiar with the clinical signs and symptoms to determine efficacy of the antibody immunotherapy. In some patients antibody treatments are cleared faster than in others, in particular if patients have different allotypes (constant region polymorphisms).

One aspect of the present invention includes a method of providing an immunotherapy to a patient comprising administering to the patient a therapeutic antibody and detecting the presence of anti-PD-1 and/or anti-PD-L1 therapeutic antibodies using the fusion proteins described herein. It is envisioned that these methods can be used to monitor the efficacy of antibody-based therapy. In one embodiment, a physician may wish to increase dose if efficacy is slow to appear and is not removing symptoms. These tools we describe herein will allow sensitive detection of the expected change in circulating levels of therapeutic antibody.

In further embodiments, the present invention provides methods for detecting and/or monitoring diseases mediated by PD-1 and/or PD-L1 by measuring anti-PD-1 and/or anti-PD-L1 therapeutic antibodies. Said methods for detecting and/or monitoring diseases mediated by PD-1 and/or PD-L1 comprises contacting a sample from a patient with a fusion protein described herein. In further embodiments, the methods for detecting and/or monitoring diseases mediated by PD-1 and/or PD-L1 is conducted on a patient that has undergone a course of immunotherapy with a therapeutic antibody.

Some aspects of the present invention relate to a method of determining the amount of circulating levels of a biotherapeutic antibody selected from the group consisting of nivolumab, pembrolizumab and other anti-PD-1 therapies. In some embodiments, the method of determining the amount of circulating levels of a biotherapeutic antibody comprise the steps of (i) obtaining a sample from a patient undergoing the antibody treatment, and (ii) contacting the sample with the fusion protein according to the present invention.

Other aspects of the present invention relate to a method of determining the amount of (free) circulating levels of a biotherapeutic antibody selected from the group consisting of Atezolizumab, Avelumab, and other anti-PD-L1 therapies, comprising (i) obtaining a sample from a patient undergoing the antibody treatment, and (ii) contacting the sample with the fusion protein according to the present invention.

Some embodiments are related to a composition comprising a fusion protein comprising PD-1 and/or PD-L1, or a fragment thereof, and an oligomerization domain. Further provided herein is a method of making a composition comprising a fusion protein comprising PD-1 and/or PD-L1 or a fragment thereof and an oligomerization domain as described herein. A kit comprising the fusion protein or the composition is also provided.

Some embodiments include an immunoassay reagent comprising a fusion protein as described herein for assaying a composition containing anti-PD-1 and/or anti-PD-L1 antibodies. The immunoassay reagent may be bound to a solid support. A solid support may be, for example, a bead, membrane, microtiter plate, polypeptide chip, or the solid-phase of a chromatography column.

Various embodiments also include a device for assaying a composition containing anti-PD-1 and/or anti-PD-L1 antibodies. The device may be a device for determining whether a sample contains anti-PD-1 and/or anti-PD-L1 antibodies. Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

The invention will be more fully understood by reference to the following examples. They should not, however, be construed as limiting the scope of this invention. All literature and patent citations mentioned herein are expressly incorporated by reference.

EXAMPLES

Example 1: Expression and Purification of Checkpoint Proteins

Genes encoding the various fusion protein of human PD-1 and PD-L1 were synthetically produced, codon optimized for mammalian expression, and cloned into either pTT5 vector or other high expressing mammalian vector. Low endotoxin scale-up preparations of plasmid DNA were performed to prepare for transient mammalian expression.

Cultures of Human embryonic kidney (HEK) 293 derivative cells were transiently transfected with scaled-up expression plasmids and grown, utilizing standard transfection protocol. Cell pellets were harvested by centrifugation and protein expression in the cell culture supernatant (CCS) was verified by western blot and SDS-PAGE 4-5 days post-transfection.

Fusion proteins comprising IgG1 or IgG2a were purified by Protein A affinity chromatography and formulated via dialysis, aliquoted, and stored at −80° C. Proteins containing the p53 multimerization domains had a C-terminal histidine tag and were purified by immobilized metal affinity chromatography, buffer exchanged, aliquoted, and stored at −80° C. Protein expression and confirmation of tetramerization was assessed by SDS-PAGE, and CE-SDS (PD-1-p53-His).

Figure 2:
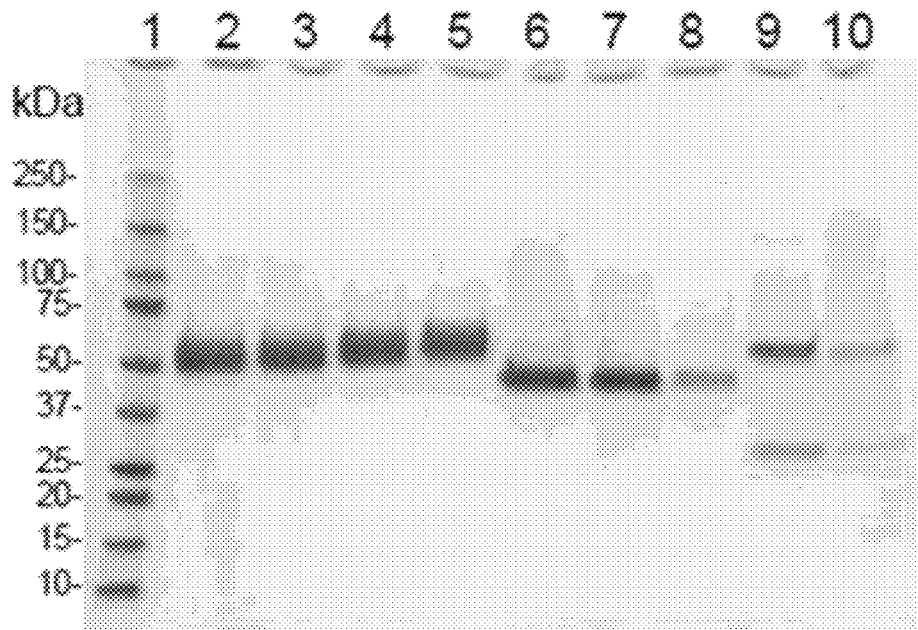
FIG. 2—Represents SDS-PAGE chromatography of various fusion proteins post expression and purification with a non-reducing 4-20% Tris-glycine TGX gel FIG. 3A—Shows specific reactivity of a recombinant PD-1 fusion protein against anti-PD-1 antibody in a serial dilution series (dilutions from 0.5 µg/ml to 0.04 µg/ml).

FIGS. 1 and 2 show 4-20% tris-glycine TGX™ SDS-PAGE gels run under reducing and non-reducing conditions, respectively. The gels were stained with the InstantBlue™ protein stain. The lanes of each gel are numbered 1 to 10 from left to right. The first lane contains a molecular weight marker, lanes 2-5 contain fusion proteins corresponding to SEQ ID NO: 14 to 17 and lanes 6 to 8 contain fusion proteins corresponding to SEQ ID NO: 21 to 23, which were cloned and then expressed in eukaryotic cells. Each fusion protein was capable of expression at a detectable level.

Example 2: Specificity of PD-1 and PD-L1 Recombinant Proteins

2a. Specific Reactivity Against Anti-PD-1 and Anti-PD-L1 Antibodies

Several recombinant PD-1 and PD-L1 proteins were tested for their specific reactivity against anti-PD-1 and anti-PD-L1 antibodies from commercial sources. Recombinant versions of PD-L1 and PD-1 proteins were tested separately with directly labeled fluorescent antibodies using ELISA assays.

Figure 3A:
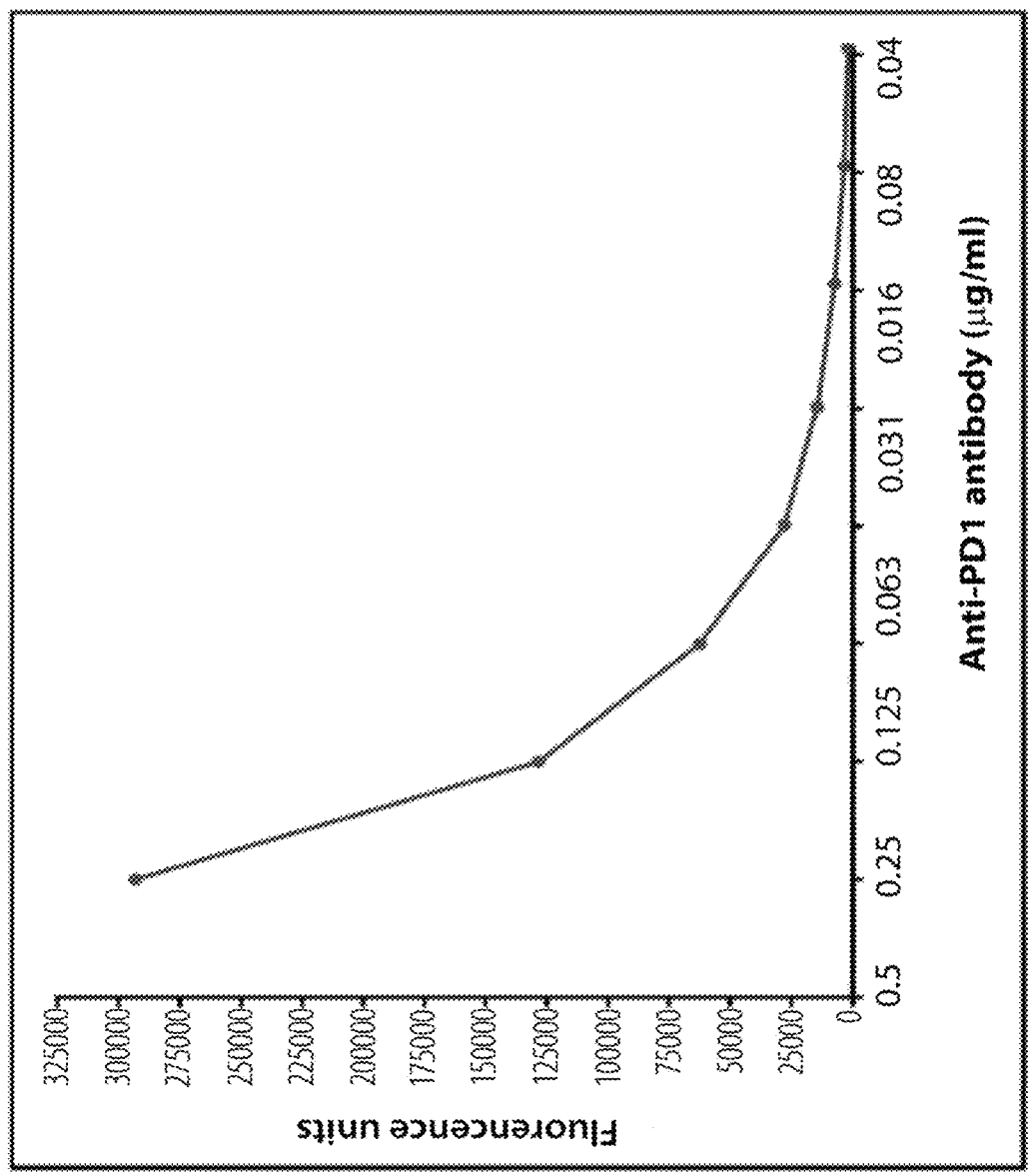
FIG. 3B—Shows specific reactivity of recombinant PD-L1 fusion proteins against anti-PD-L1 antibody in a dilution series as mentioned above. The figure also shows a comparison of the reactivity of PD-L1-Fc monomer and PD-L1-p53 tetramer.
Figure 3B:
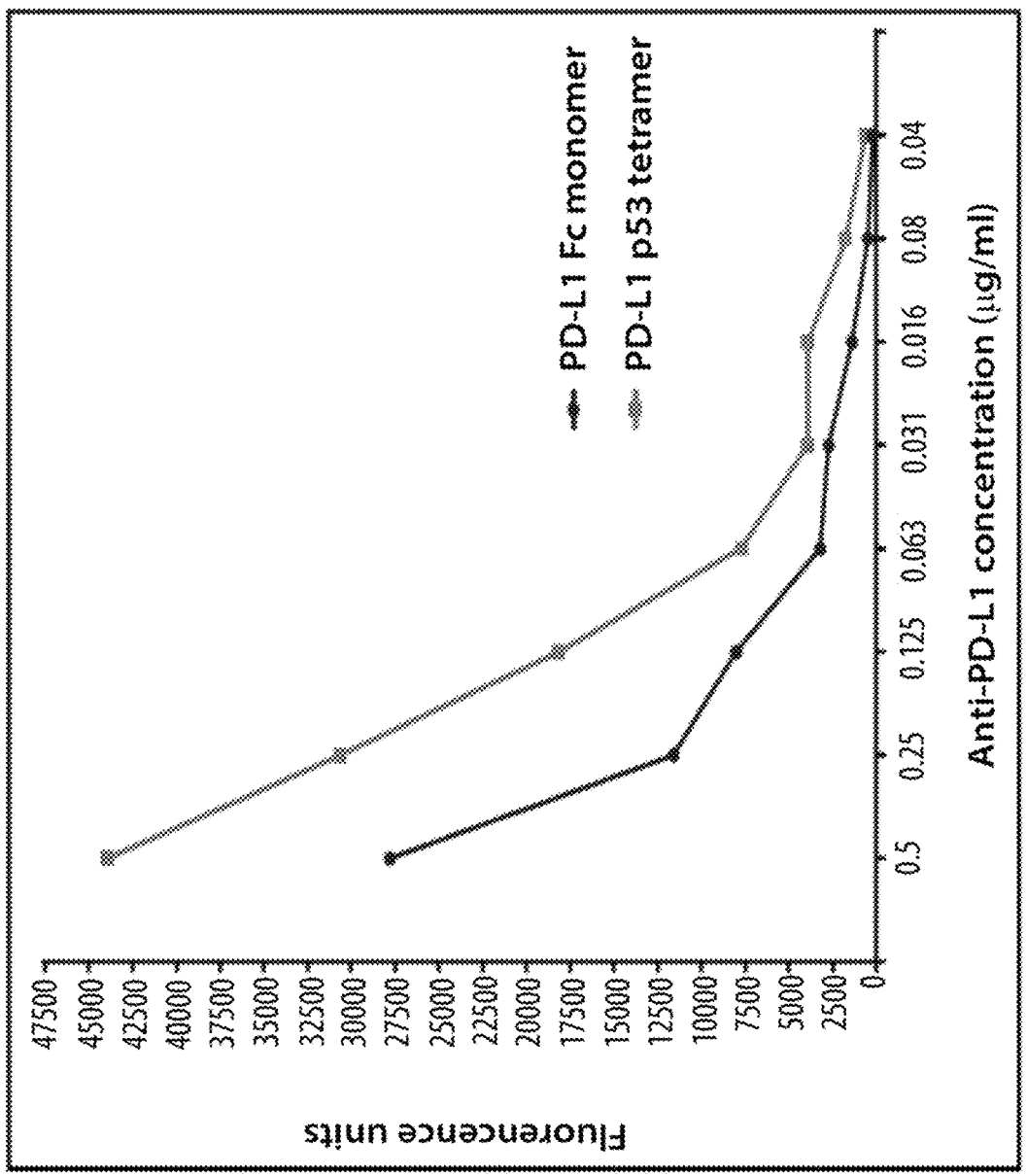

ELISA plates were coated with PD-1 or PD-L1 fusion proteins and detected with APC conjugated anti-PD-1 or anti-PDL-1 antibodies using a fluorescent reader. The different antigens and different versions of the same antigen were tested at equimolar concentrations, 50 nM to compensate for the different MW of the proteins. FIG. 3A shows specific reactivity of PD-1-p53 (PD1-(GGGPS)2-p53-HisTag, SEQ ID NO:29) against anti-PD-1 antibody in a serial dilution series (dilutions from 0.5 µg/ml to 0.04 µg/ml). FIG. 3B shows specific reactivity of PD-L1-p53 proteins (PD-L1-(GGGPS)2-p53-HisTag, SEQ ID NO: 30) against anti-PD-1 antibody in a dilution series as mentioned above. FIG. 3B also shows a comparison of the reactivity of PD-L1 Fc monomer (SEQ ID NO:22) and PD-L1 p53 tetramer (SEQ ID NO:30).

2b. Comparison of PD-1 Fusion Proteins for Quantification of Anti-PD1 Antibodies in Human Plasma The recombinant proteins PD1-(GGGPS)2-IgG1-Fc (CH2, CH3 only) (SEQ ID.14), PD1-IgG1-Fc (SEQ ID.16) and PD1-p53 (SEQ ID NO:29) were tested for detection of anti-PD1 therapeutic mAbs used for cancer treatment as well as for determination of the anti-PD1 mAb drug concentration in the human plasma; in this case Pembrolizumab (Keytruda®) was used.

ELISA plates were coated overnight with several PD-1 fusion proteins diluted in PBS, p.H. 7.4 as a coating buffer at a concentration of 50 nM. The next day, plates were washed five times with 1×ELISA Wash buffer (BioRad, BUF031C). A blocking step was initiated by adding 200 µL of 1:4 BlockACE (BioRad, BUF029) water solution, prepared according to the instructions of the manufacturer. Plates were incubated for one hour at 37° C.; after another washing step. Hundred microliters of each Pembrolizumab standard concentration, as well as an IgG1 negative control, were diluted in Assay buffer (1:8 BlockACE water solution) and added to each well. Plates were incubated for one hour at 37° C. and then washed five times with 1×ELISA wash buffer as previously described. Following this step, 100 µL of 0.5 µg/mL whole mouse anti-human IgG4, Fc specific-conjugated with horseradish peroxidase antibody were added to each well (Thermoscientific, clone HP6023 cat. no. A-10654). Plates were incubated for thirty minutes at 37° C.; washed five times in 1×ELISA wash buffer and optical density was measured at 15, 30 and 60 min; following addition of ABTS substrate (Roche, cat. no. 11 684 302 001).

Figure 4A:
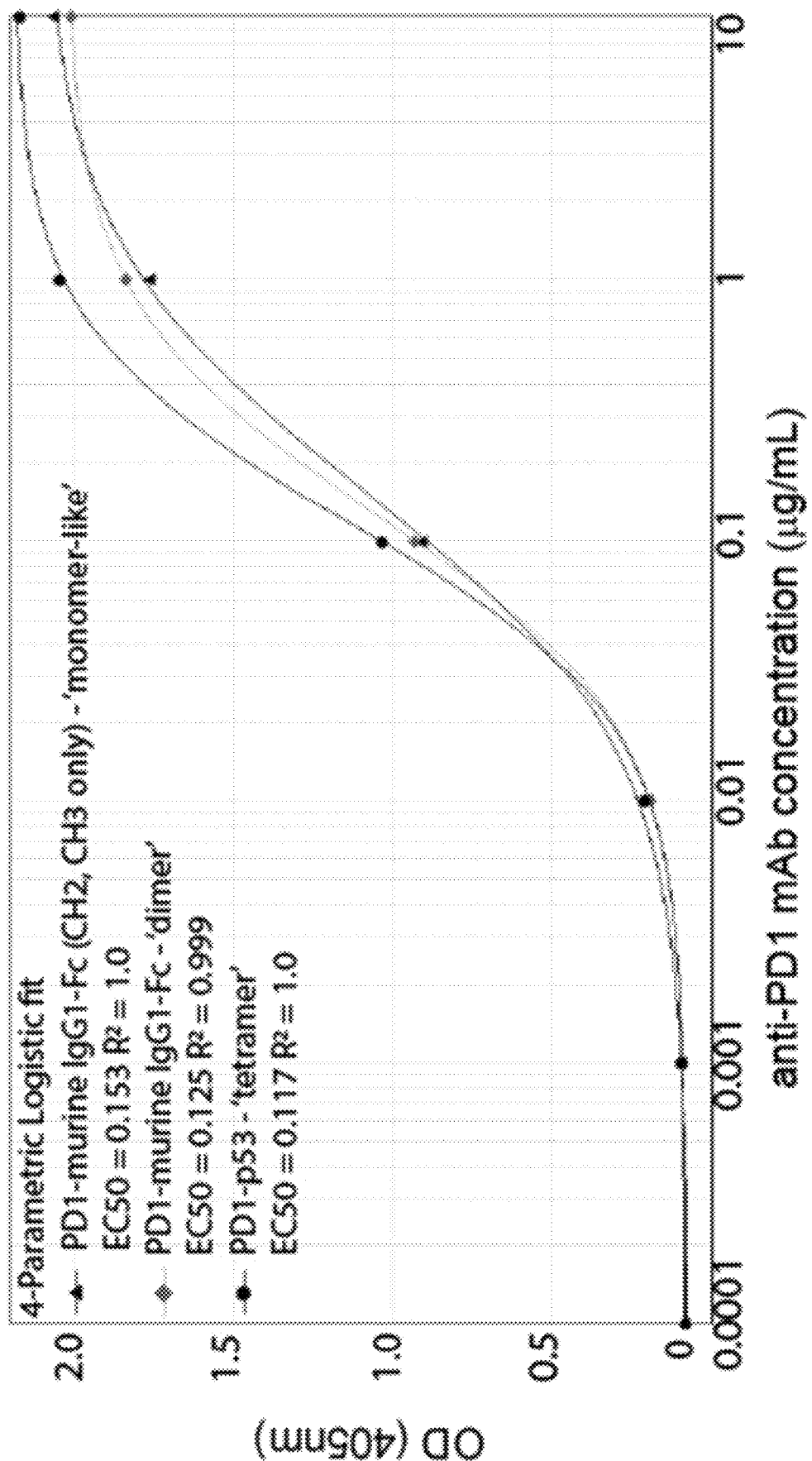
FIG. 4A—Shows a comparison of various PD-1 fusion proteins for quantification of anti-PD-1 antibodies (pembrolizumab) in human plasma.
Figure 4B:
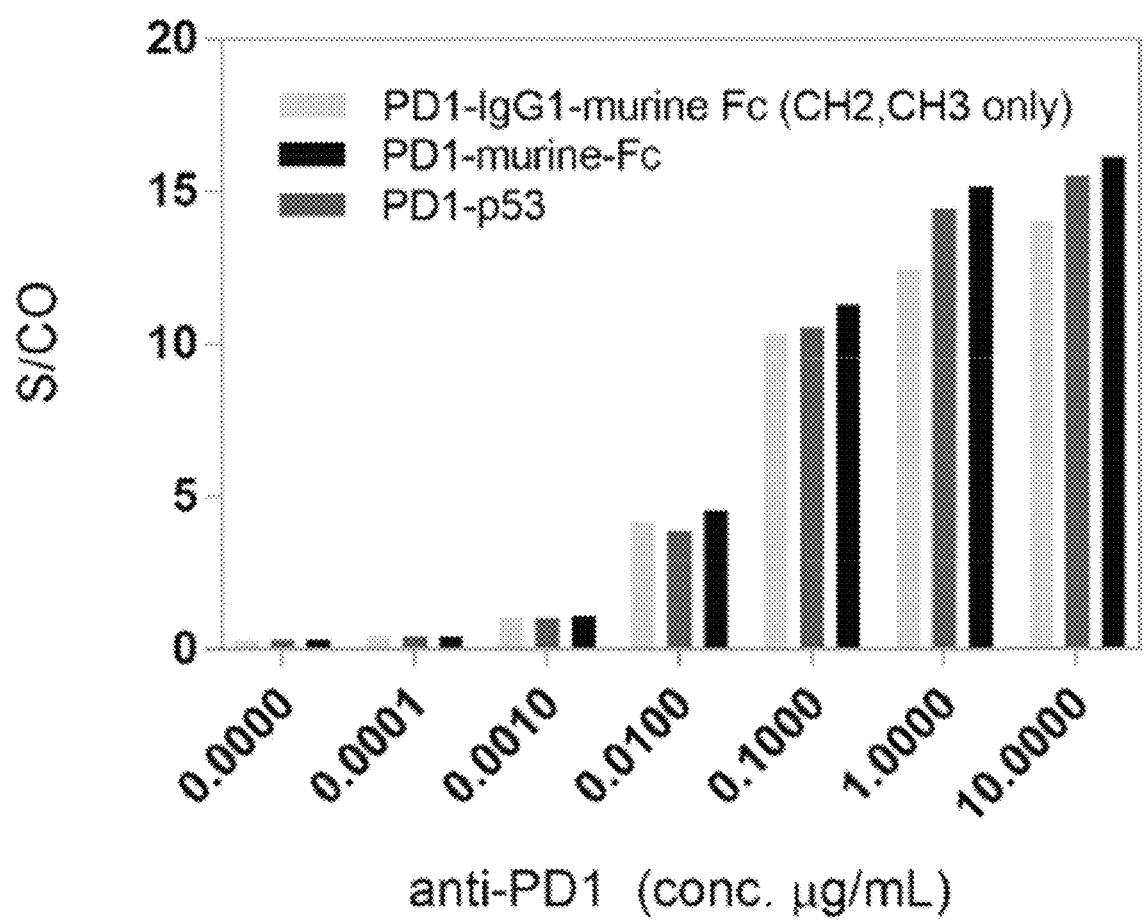
FIG. 4B—Shows the signal to cut off noise of various PD-1 fusion proteins for quantification of anti-PD-1 antibodies (pembrolizumab) in human plasma.

FIG. 4A show the use of PD-1 recombinant proteins to determine the concentrations of Pembrolizumab in human plasma. Pembrolizumab standards at six concentrations (10 µg/mL, 1 µg/mL, 0.1 µg/mL, 0.01 µg/ml, 0.001 µg/mL, and 0.0001 ug/mL) were used to generate a standard curve for each of the recombinant PD1 proteins generated. The PD1 proteins tested are present at different oligomeric states, 'monomer-like', dimer and tetramer. The data shows that PD1-p53 (tetramer) has higher avidity and lower EC50 value than PD1-Fc (dimer) and PD1-Fc (CH2, CH3) ('monomer'). In addition, using PD1-p53 provides an improved S/CO (signal to cut off noise) from concentrations ranging from 0.01-10 µg/ml (FIG. 4B). In this assay the cut-off value was determined by the mean of three negative plasma samples plus three times the standard deviation of the optical densities obtained for these samples.

2c. Reactivity of PD-L1 Recombinant Proteins

Figure 5:
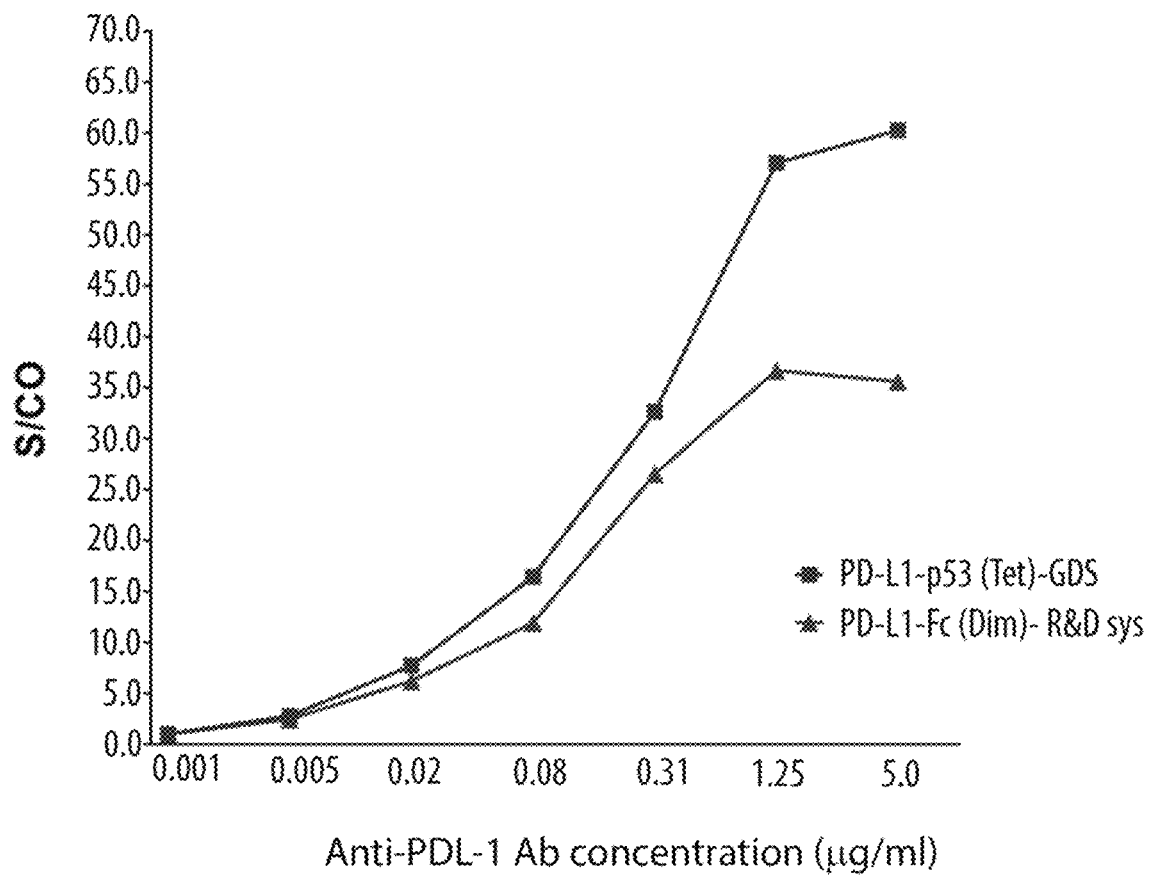
FIG. 5—Shows specific reactivity of various PD-L1 fusion proteins against anti-PD-L1 antibodies.

Different PD-L1 fusion proteins were tested for their reactivity against a specific anti-PD-L1 antibody. Recombinant versions of PD-L1 (PD-L1-p53 tetramer (SEQ ID NO:30) and PD-L1-Fc dimer (R&D systems)) were tested with fluorescently labeled anti-PD-L1 mAb. Briefly, ELISA plates (black) were coated with different PD-L1 proteins in equimolar concentrations, 20 nM and detected directly with APC conjugated anti-PDL-1 antibody using a fluorescent reader. FIG. 5 shows the comparison of PD-L1 Fc dimer (R&D sys) and PD-L1 p53 tetramer (SEQ ID NO:30) reactivity against anti-PD-L1 antibody in a serial dilution series (4 fold dilutions from 5 µg/ml to 0.001 µg/ml) and the signal to cut off to concentrations is depicted. The PD-L1 p53 tetramer showed higher binding reactivity than the PD-L1-Fc dimer.

REFERENCES

1. Goodman, Patel & Kurzrock, PD-1-PD-L1 immune-checkpoint blockade in B-cell lymphomas, Nature Reviews Clinical Oncology, 14:203-220, 2017.
2. Elassaiss-Schaap et al., Using Model-Based "Learn and Confirm" to Reveal the Pharmacokinetics-Pharmacodynamics Relationship of Pembrolizumab in the KEYNOTE-001 Trial CPT Pharmacometrics Syst. Pharmacol. (2017) 6, 21-28; doi:10.1002/psp4.12132.
3. Agrawal et al. Nivolumab dose selection: challenges, opportunities, and lessons learned for cancer immunotherapy. Journal for ImmunoTherapy of Cancer (2016) 4:72 DOI 10.1186/s40425-016-0177-2
4. Gardiner et al., A Randomized, Double-Blind, Placebo-Controlled Assessment of BMS-936558, a Fully Human Monoclonal Antibody to Programmed Death-1 (PD-1), in Patients with Chronic Hepatitis C Virus Infection. PLoS ONE, https://doi.org/10.1371/journal.pone.0063818 2013.
5. Zheng et al., Level of circulating PD-L1 expression in patients with advanced gastric cancer and its clinical implications. Chin Journal of Cancer Research, 26, 104-111, 2014.
6. Ono Pharmaceutical Co. Ltd. (2014), Human Anti-human PD-1 Monoclonal Antibody "OPDIVO® Intravenous Infusion 20 mg/100 mg" Receives Manufacturing and Marketing Approval in Japan for the Treatment of Unresectable Melanoma [press release]. Retrieved from http://www.ono.co.jp/eng/news/pdf/sm_cn140704.pdf.]
7. Bristol-Meyers Squibb (2016), Opdivo® (nivolumab) Granted First Approval of a PD-1 Inhibitor in Hematology for the Treatment of Classical Hodgkin Lymphoma Patients Who Have Relapsed or Progressed After Auto-HSCT and Post-transplantation Brentuximab Vedotin by the FDA1 [press release]. Retrieved from https://news.bms.com/press-release/cancer/opdivo-nivolumab-qranted-first-approval-pd-1-inhibitor-hematology-treatment-cla
8. Federal Drug Administration (2014), FDA expands approved use of Opdivo to treat lung cancer, [press announcement]. Retrieved from https://www.fda.gov/NewsEvents/newsroom/PressAnnouncements/ucm436534.htm
9. Federal Drug Administration (2015), FDA approves Opdivo to treat advanced form of kidney cancer, [press announcement]. Retrieved from https://www.fda.gov/NewsEvents/Newsroom/PressAnnouncements/ucm473971.htm
10. Federal Drug Administration (2017), FDA grants accelerated approval to pembrolizumab for first tissue/site agnostic indication [press announcement]. Retrieved from https://www.fda.gov/Drugs/InformationOnDrugs/ApprovedDrugs/ucm560040.htm
11. Thompson R H, Gillett M D, Cheville J C, Lohse C M, Dong H, Webster W S, Krejci K G, Lobo J R, Sengupta S, Chen L, Zincke H, Blute M L, Strome S E, Leibovich B C, Kwon E D (2004). Costimulatory B7-H1 in renal cell carcinoma patients: Indicator of tumor aggressiveness and potential therapeutic target. PNAS USA. 101 (49): 17174-9. doi:10.1073/pnas.0406351101
12. Opdivo (package insert), Bristol-Meyers Squibb, New York, N.Y.; 2017.

13. Pembrolizumab (package insert), Merck, Kelinworth, N.J.; 2017.
14. Ybe J A, Fontaine S N, Stone T, Nix J, Lin X, and S Mishra. 2013 Nuclear localization of clathrin involves a labile helix outside the trimerization domain. FEBS Lett. 2013 Jan. 16; 587(2): 142-149. doi:10.1016/j.febslet.2012.11.005
15. Yang X, Lee J, Mahony E M, Kwong P D, Wyatt R, and J Sodroski. 2002. Highly Stable Trimers Formed by Human Immunodeficiency Virus Type 1 Envelope Glycoproteins Fused with the Trimeric Motif of T4 Bacteriophage Fibritin J Virology p. 4634-4642 Vol. 76, No. 9
16. Lee W, Harvey T S, Yin Y, Yau P, Litchfield D, and C H Arrowsmith. 1994. Solution structure of the tetrameric minimum transforming domain of p53 Nature Structural Biology 1, 877-890
17. Lee J Y, Lee, H T, Shin W, Chae J, Kin S H, Lim H, Heo T W, Park K Y, Lee Y J, Ruy S E, Lee J U, Heo Y S. Structural Bassi of checkpoint blockade by monoclonal antibodies in cancer immunotherapy. et al, Nat. Commun, 2016, 7:13354.
18. Brahmer J R, Drake C G, Wollner I, Powderly J D, Picus J, Sharfman W H, Stankevich E, Pons A, Salay T M, McMiller T L, Gilson M M, Wang C, Selby M, Taube J M, Anders R, Chen L, Korman A J, Pardoll D M, Lowy I, Topalian S L. Phase I study of single-agent anti-programmed death-1 (MDX-1106) in refractory solid tumors: safety, clinical activity, pharmacodynamics, and immunologic correlates. J Clin Oncol. 2010 Jul. 1; 28(19):3167-75.
19. Farolfi A, Schepisi G, Conteduca V, Burgio S L, Lolli C, De Giorgi U. Pharmacokinetics, pharmacodynamics and clinical efficacy of nivolumab in the treatment of metastatic renal cell carcinoma. Expert Opin Drug Metab Toxicol. 2016 September; 12(9):1089-96.
20. Jefferis R, Lefranc M P. Human immunoglobulin allotypes: possible implications for immunogenicity. MAbs. 2009 July-August; 1(4):332-8.
21. Ternant D, Arnoult C, Pugniére M, Dhommée C, Drocourt D, Perouzel E, Passot C, Baroukh N, Mulleman D, Tiraby G, Watier H, Paintaud G, Gouilleux-Gruart V. IgG1 Allotypes Influence the Pharmacokinetics of Therapeutic Monoclonal Antibodies through FcRn Binding. J Immunol. 2016 Jan. 15; 196(2):607-13.
22. Webster C I, Bryson C J, Cloake E A, Jones T D, Austin M J, Karle A C, Spindeldreher S, Lowe D C, Baker MP A comparison of the ability of the human IgG1 allotypes G1 m3 and G1 m1,17 to stimulate T-cell responses from allotype matched and mismatched donors. MAbs. 2016; 8(2):253-63.
23. Dempke W C M, Fenchel K, Uciechowski P, Dale S P. Second- and third-generation drugs for immuno-oncology treatment—The more the better? Eur J Cancer. 2017 March; 74:55-72.

The invention claimed is:

1. A fusion protein comprising:
an extracellular domain of a human Programmed Cell Death-1 (PD-1) protein, or a fragment thereof, wherein the extracellular domain or fragment thereof binds a human PD-L1 protein; and
an oligomerization domain, wherein the oligomerization domain is selected from the group consisting of a p53 tetramer domain, or a fragment of the p53 tetramer domain.

2. The fusion protein according to claim 1, wherein the extracellular domain of the PD-1 protein, or the fragment thereof, is fused to the oligomerization domain via one or more peptide linkers comprising the amino acid sequence set forth in SEQ ID NO: 5.

3. The fusion protein according to claim 1, wherein the amino acid sequence of the extracellular domain of PD-1 is selected from the group consisting of:
(i) the amino acid sequence that shares at least 70% homology with the amino acid sequence consisting of residues 21 to 170 of SEQ ID NO:1;
(ii) the amino acid sequence that shares at least 70% homology with the amino acid sequence consisting of residues 21 to 145 of SEQ ID NO:1;
(iii) the amino acid sequence that shares at least 70% homology with the amino acid sequence consisting of residues 33 to 170 of SEQ ID NO:1;
(iv) the amino acid sequence that shares at least 70% homology with the amino acid sequence consisting of residues 33 to 145 of SEQ ID NO: 1;
(v) the amino acid sequence that shares at least 70% homology with the amino acid sequence consisting of residues 35 to 170 of SEQ ID NO:1; and
(iv) the amino acid sequence that shares at least 70% homology with the amino acid sequence consisting of residues 35 to 145 of SEQ ID NO:1.

4. The fusion protein according to claim 1, wherein the amino acid sequence of the extracellular domain of PD-1 comprises a sequence with at least 70% homology with the amino acid sequence set forth in SEQ ID NO: 12.

5. The fusion protein according to claim 1, wherein the PD-1 is recombinant PD-1.

6. A method of determining the amount of circulating levels of a biotherapeutic antibody selected from the group consisting of nivolumab, pembrolizumab and other anti-PD-1 therapies, comprising (i) obtaining a sample from a patient undergoing the antibody treatment, and (ii) contacting the sample with the fusion protein according to claim 1.

7. The fusion protein according to claim 1, wherein the extracellular domain of the PD-1 protein, or the fragment thereof, is fused to the p53 tetramer domain or the fragment of the p53 tetramer domain has a higher reactivity against an anti-PD1 antibody compared to the monomer or dimer oligomerization domain.

* * * * *

UNITED STATES PATENT AND TRADEMARK OFFICE
CERTIFICATE OF CORRECTION

| | |
|---|---|
| PATENT NO. | : 11,919,938 B2 |
| APPLICATION NO. | : 16/321385 |
| DATED | : March 5, 2024 |
| INVENTOR(S) | : Jody Berry et al. |

It is certified that error appears in the above-identified patent and that said Letters Patent is hereby corrected as shown below:

On the Title Page

Page 2, Column 2 (item (56) U.S. Patent Documents), Line 16, delete "Kelinworth," and insert -- Kenilworth, --.

In the Specification

Column 8, Line 44, delete "gel" and insert -- gel. --.

Column 8, Line 67, delete "Q9NZQ7)" and insert -- Q9NZQ7). --.

Column 12, Line 41-42, delete "G1 m3:Km3" and insert -- G1m3:Km3 --.

Column 12, Line 44, delete "allotypy" and insert -- allotype --.

Column 12, Line 51, delete "allotypy" and insert -- allotype --.

Column 13, Line 66, delete "(Gin," and insert -- (Gln, --.

Column 15, Line 24, delete "cancer" and insert -- cancer. --.

Column 15, Line 37-38, delete "leukencephalopathy" and insert -- leukoencephalopathy --.

Column 19, Line 31, delete "$_{PD-1}$K131" and insert -- $_{PD-1}$K131, --.

Column 19, Line 41, delete "$_{PD-1}$I128," and insert -- $_{PD-1}$L128, --.

Column 19, Line 49, delete "$_{PD-1}$I128," and insert -- $_{PD-1}$L128, --.

Column 19, Line 54, delete "$_{PD-1}$I128," and insert -- $_{PD-1}$L128, --.

Signed and Sealed this
Ninth Day of July, 2024

*Katherine Kelly Vidal*
Katherine Kelly Vidal
*Director of the United States Patent and Trademark Office*

CERTIFICATE OF CORRECTION (continued)
U.S. Pat. No. 11,919,938 B2

Column 23, Line 28, delete "linkers" and insert -- linkers. --.

Column 28, Line 64, delete "(PD1-(GGGPS)" and insert -- (PD-1-(GGGPS) --.

Column 29, Line 8, delete "(PD1-(GGGPS)" and insert -- (PD-1-(GGGPS) --.

Column 29, Line 9, delete "PD1-IgG1-Fc" and insert -- PD-1-IgG1-Fc --.

Column 29, Line 10, delete "PD1-p53" and insert -- PD-1-p53 --.

Column 29, Line 11, delete "anti-PD1 therapeutic" and insert -- anti-PD-1 therapeutic --.

Column 29, Line 12, delete "of the anti-PD1 mAb" and insert -- of the anti-PD-1 mAb --.

Column 29, Line 47, delete "PD1-p53 (tetramer) has" and insert -- PD-1-p53 (tetramer) has --.

Column 29, Line 48-49, delete "value than PD1-Fc (dimer) and PD1-Fc (CH2, CH3) ('monomer'). In Addition, using PD1-p53 provides" and insert -- value than PD-1-Fc (dimer) and PD-1-Fc (CH2, CH3) ('monomer'). In Addition, using PD-1-p53 provides --.

Column 30, Line 18, delete "-2" and insert -- -2. --.

Column 30, Line 42, delete "qranted" and insert -- granted --.

Column 30, Line 65, delete "0406351101" and insert -- 0406351101. --.

Column 31, Line 1, delete "Kelinworth," and insert -- Kenilworth, --.

Column 31, Line 7, delete "11.005" and insert -- 11.005. --.

Column 31, Line 12, delete "9" and insert -- 9. --.

Column 31, Line 16, delete "877-890" and insert -- 877-890. --.